United States Patent
Bao et al.

(10) Patent No.: US 12,318,271 B2
(45) Date of Patent: Jun. 3, 2025

(54) WEARABLE ARTICLE COMPRISING AN ELASTIC LAMINATE HAVING GOOD WICKING PROPERTIES

(71) Applicant: The Procter & Gamble Company, Cincinnati, OH (US)

(72) Inventors: Zheng Bao, Beijing (CN); Koichi Morimoto, Shunyi District Beijing (CN); Hui Liu, Beijing (CN); Rodrigo Rosati, Frankfurt am Main (DE)

(73) Assignee: The Procter & Gamble Company, Cincinnati, OH (US)

( * ) Notice: Subject to any disclaimer, the term of this patent is extended or adjusted under 35 U.S.C. 154(b) by 634 days.

(21) Appl. No.: 17/528,491

(22) Filed: Nov. 17, 2021

(65) Prior Publication Data

US 2022/0079817 A1    Mar. 17, 2022

Related U.S. Application Data

(63) Continuation of application No. PCT/CN2020/106128, filed on Jul. 31, 2020.

(51) Int. Cl.
     *A61F 13/49*      (2006.01)
     *B32B 5/26*      (2006.01)
     (Continued)

(52) U.S. Cl.
     CPC .......... *A61F 13/4902* (2013.01); *B32B 5/266* (2021.05); *B32B 7/09* (2019.01);
     (Continued)

(58) Field of Classification Search
     CPC .......... A61F 13/15203; A61F 13/49058; A61F 13/4906; A61F 13/49061; A61F 2013/15487; A61F 2013/15504; A61F 2013/15536; A61F 2013/49025; A61F 2013/51038; A61F 2013/51042
     See application file for complete search history.

(56) References Cited

U.S. PATENT DOCUMENTS

| | | |
|---|---|---|
| 8,282,617 B2 | 10/2012 | Kaneda |
| 8,777,918 B2 | 7/2014 | Kuwano et al. |

(Continued)

FOREIGN PATENT DOCUMENTS

| | | |
|---|---|---|
| CN | 1299261 A | 6/2001 |
| CN | 102316838 A | 1/2012 |

(Continued)

OTHER PUBLICATIONS

PCT Suppl. Search Report and Written Opinion for PCT/CN2020/106128 dated Nov. 11, 2022, 06 pages.

(Continued)

*Primary Examiner* — Catharine L Anderson
(74) *Attorney, Agent, or Firm* — Charles R. Matson

(57) ABSTRACT

The invention relates to a wearable article comprising an elastic laminate. The elastic laminate comprises a first web and a second web being in a face to face relationship with each other. The first web is a nonwoven web having a vertical wicking height after 60 seconds of less than 5 mm according to the test method set out herein. The second web is a nonwoven web having a vertical wicking height after 60 seconds of at least 5 mm.

17 Claims, 4 Drawing Sheets

(51) Int. Cl.
  *B32B 7/09* (2019.01)
  *A61F 13/15* (2006.01)
(52) U.S. Cl.
  CPC . *A61F 2013/15487* (2013.01); *B32B 2262/02* (2013.01); *B32B 2262/06* (2013.01); *B32B 2262/144* (2021.05); *B32B 2307/728* (2013.01); *B32B 2555/02* (2013.01)

(56) References Cited

U.S. PATENT DOCUMENTS

| | | | |
|---|---|---|---|
| 8,840,600 | B2 | 9/2014 | Takeuchi |
| 8,932,274 | B2 | 1/2015 | Mukai |
| 9,622,922 | B2 | 4/2017 | Nelson |
| 9,633,933 | B2 | 4/2017 | Hayashi |
| 10,064,763 | B2 | 9/2018 | Takahashi et al. |
| 11,033,441 | B2 | 6/2021 | Xu et al. |
| 11,612,521 | B2 | 3/2023 | Ishikawa |
| 11,833,018 | B2 | 12/2023 | Dalal et al. |
| 2003/0065298 | A1 | 4/2003 | Krishnaswamy-Mirle |
| 2003/0208175 | A1* | 11/2003 | Gross .............. A61F 13/534 604/378 |
| 2006/0047260 | A1 | 3/2006 | Ashton |
| 2010/0191207 | A1 | 7/2010 | Oba et al. |
| 2010/0310837 | A1 | 12/2010 | Bond et al. |
| 2010/0310845 | A1* | 12/2010 | Bond .............. D04H 3/16 442/337 |
| 2010/0312208 | A1 | 12/2010 | Bond et al. |
| 2010/0312212 | A1 | 12/2010 | Bond et al. |
| 2012/0238170 | A1 | 9/2012 | Weisman et al. |
| 2016/0332418 | A1 | 11/2016 | Jenkins et al. |
| 2019/0274895 | A1 | 9/2019 | Chen et al. |
| 2023/0190541 | A1 | 6/2023 | Morimoto et al. |

FOREIGN PATENT DOCUMENTS

| | | |
|---|---|---|
| CN | 107920924 A | 4/2018 |
| CN | 110072499 A | 7/2019 |
| CN | 110087600 A | 8/2019 |
| JP | 2006326221 A | 12/2006 |
| JP | 2017113186 A | 6/2017 |
| JP | 6411323 B2 | 10/2018 |
| WO | 2010110154 A1 | 9/2010 |
| WO | 2019169989 A1 | 9/2019 |

OTHER PUBLICATIONS

All Office Actions; U.S. Appl. No. 17/527,543, filed Nov. 16, 2021.
All Office Actions; U.S. Appl. No. 17/528,316, filed Nov. 17, 2021.
All Office Actions; U.S. Appl. No. 17/529,778, filed Nov. 18, 2021.
PCT Search Report and Written Opinion for PCT/CN2020/106128 dated Apr. 29, 2021.
Unpublished U.S. Appl. No. 17/527,543, filed Nov. 16, 2021, to first inventor et al.
Unpublished U.S. Appl. No. 17/528,316, filed Nov. 17, 2021, to first inventor et al.
Unpublished U.S. Appl. No. 17/529,778, filed Nov. 18, 2021, to first inventor et al.

* cited by examiner

WEARABLE ARTICLE COMPRISING AN ELASTIC LAMINATE HAVING GOOD WICKING PROPERTIES

CROSS REFERENCE TO RELATED APPLICATION

This application is a continuation, under 35 USC 120, of PCT Application No. PCT/CN2020/106128, filed on Jul. 31, 2020, which is incorporated herein by reference.

FIELD OF THE INVENTION

The present invention relates to a wearable article comprising an elastic laminate suitable for use in wearable articles which exhibits improved sweat management properties.

BACKGROUND OF THE INVENTION

Substrate materials such as nonwoven fabrics and laminates thereof, are commonly used for wearable articles such as absorbent articles. For example, absorbent articles typically use nonwoven substrate materials for both the skin facing side as well as the garment facing side of the articles, to control the movement of liquids and to provide a comfortable, conforming fit when the article is worn by a wearer. By comfortableness, what may be desired is a cloth-like substrate which is capable of effectively absorbing sweat and excess moisture from the skin and releasing them outside the article. Such is particularly desired for absorbent articles by caregivers of young children, wherein skin health is closely associated with the absence of heat rashes and diaper rashes. Heat rashes in the waist area may be associated with wetness or dampness in the waist area inside an absorbent article. It is a common practice for caregivers to check the degree of wetness or dampness by touching the waist area inside the absorbent article worn by a young child.

Elastic laminates having sweat management properties have been proposed, such as those described in Japanese Patent Application publications 2017-12319A and 2017-113186A. There is a need to provide elastic laminates with further improved sweat management properties, while being economic to make.

Elastic laminates used, e.g. for so-called belts forming the front and back waist regions of absorbent pants are typically made of two nonwoven webs, which are joined to each other in a face to face relationship, with elastic strands sandwiched in between. In such laminates, a first nonwoven web (the inner nonwoven web) is facing the skin of the wearer and is in direct contact with the skin over a relatively large area of its surface. A second nonwoven web (the outer nonwoven web) is facing outwardly, away from the wearer, so it will commonly be in contact with the garment of the wearer. Often, the outer nonwoven web comprises an extended portion which is folded over the inner nonwoven web at the edge of the elastic laminate that forms the waist edge of the absorbent pant. Thereby, a more underwear-like, finished appearance of the pant is provided. Consequently, adjacent to the waist edge, the elastic laminate may comprise three nonwoven webs, namely the inner nonwoven web which is sandwiched between the outer nonwoven web and the extended, folded over portion of the outer nonwoven web.

The first and second nonwoven webs are typically both hydrophobic which has been found to lead to a relatively unsatisfactory performance in sweat management, i.e., in transporting sweat from the skin of the wearer through the laminate to the outside.

To address this drawback, it has been suggested to use a hydrophobic inner nonwoven web and a hydrophilic outer nonwoven web. However it has been found that this technical approach may have certain limitations in that the sweat may not be sufficiently wicked in the plane of the belt itself, remaining localized in a limited wet area, which can lead to local fluid saturation and slower evaporation rate.

There is still a need for an elastic laminate with improved ability to transport liquid away from the wearer's skin in an efficient manner.

SUMMARY OF THE INVENTION

The invention relates to a wearable article comprising an elastic laminate. The elastic laminate comprises a first web and a second web being in a face to face relationship with each other. Each of the first and second web are comprised by the complete elastic laminate. The first web is a nonwoven web having a vertical wicking height after 60 seconds of less than 5 mm according to the test method set out herein. The second web is a nonwoven web having a vertical wicking height after 60 seconds of at least 5 mm according to the test method set out herein.

DEFINITIONS

Figure 1A:
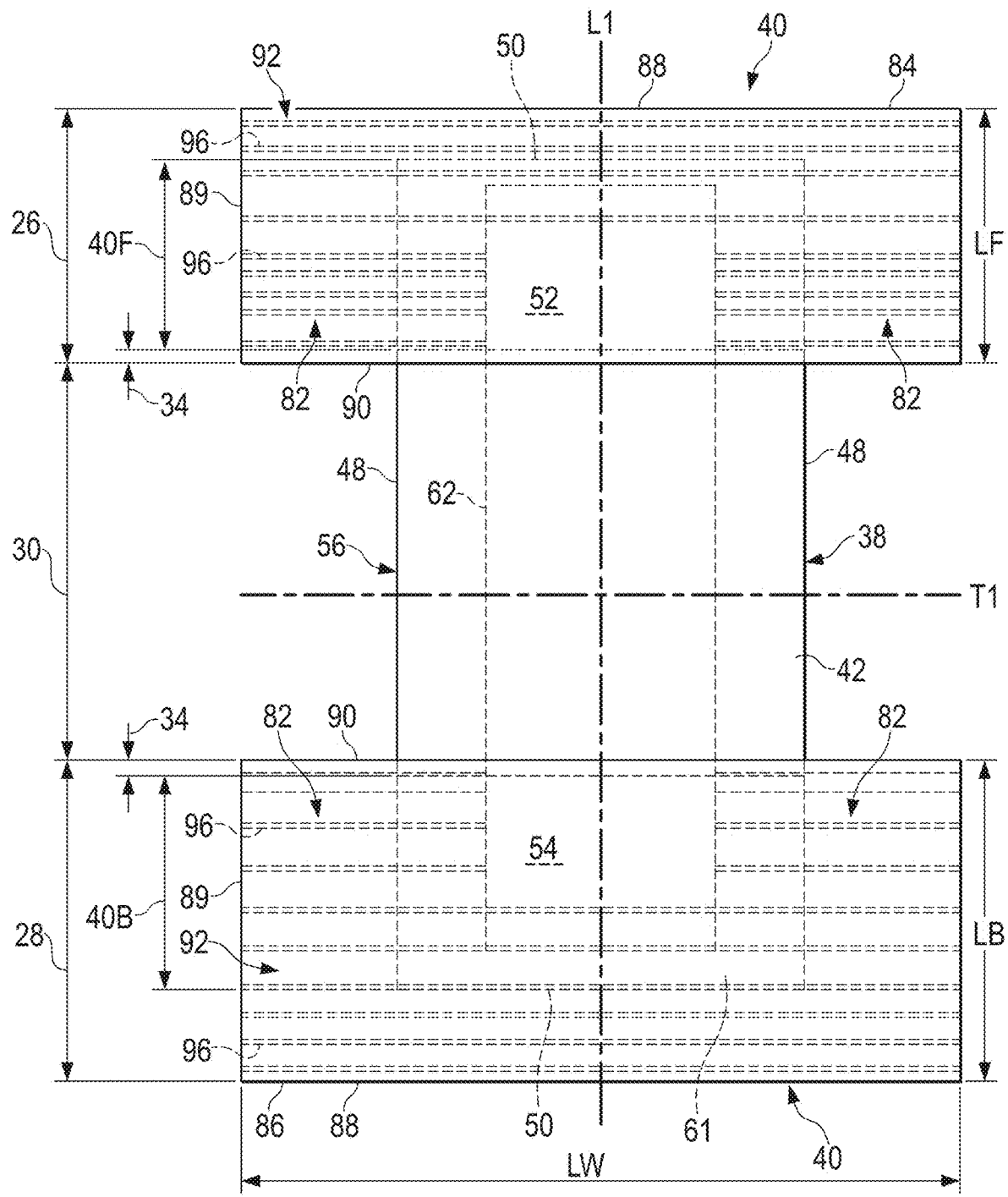
FIGS. 1A-1B are a schematic plan views of one embodiment of a wearable article of the present invention with the seams un-joined and in a flat uncontracted condition showing the garment facing surface

As used herein, the following terms shall have the meaning specified thereafter: "Wearable article" refers to articles of wear which may be in the form of pants, taped diapers, incontinent briefs, feminine hygiene garments, wound dressings, hospital garments, and the like. Preferably, the wearable article of the present invention is a pant. The "wearable article" may be so configured to also absorb and contain various exudates such as urine, feces, and menses discharged from the body. The "wearable article" may serve as an outer cover adaptable to be joined with a separable disposable absorbent insert for providing absorbent and containment function, such as those disclosed in PCT publication WO 2011/087503A.

As used herein, "taped diaper" and "pant" refers to an absorbent article generally worn by babies, infants and incontinent persons about the lower torso to encircle the waist and legs of the wearer and that is specifically adapted to receive and contain urinary and fecal waste. In a pant, as used herein, the longitudinal edges of the first and second waist region are attached to each other to a pre-formed waist opening and leg openings. A pant is generally placed in position on the wearer by inserting the wearer's legs into the leg openings and sliding the pant absorbent article into position about the wearer's lower torso. A pant may be pre-formed by any suitable technique including, but not limited to, joining together portions of the absorbent article using refastenable and/or non-refastenable bonds (i.e., with permanent side seams not intended to be torn upon prior to removal of the pant from the wearer for disposal). In a diaper, the waist opening and leg openings are only formed when the diaper is applied onto a wearer by (releasable) attaching the longitudinal edges of the first and second waist region to each other on both sides by a suitable fastening system.

"Taped diaper" refers to disposable absorbent articles which are applied on a wearer by tapes.

As used herein, "disposable" is used in its ordinary sense to mean an article that is disposed or discarded after a limited number of usage over varying lengths of time, for example, less than 20 usages, less than 10 usages, less than 5 usages, or less than 2 usages. If the disposable absorbent article is a taped diaper, a pant, sanitary napkin, sanitary pad or wet wipe for personal hygiene use, the disposable absorbent article is most often intended to be disposed after single use. The absorbent articles described herein are disposable.

"Longitudinal" refers to a direction running substantially perpendicular from a waist edge to an opposing waist edge of the article and generally parallel to the maximum linear dimension of the article. "Transverse" refers to a direction perpendicular to the longitudinal direction.

"Inner" and "outer" refer respectively to the relative location of an element or a surface of an element or group of elements. "Inner" implies the element or surface is nearer to the body of the wearer during wear than some other element or surface. "Outer" implies the element or surface is more remote from the skin of the wearer during wear than some other element or surface (i.e., element or surface is more proximate to the wearer's garments that may be worn over the present article).

"Body-facing" (also referred to as "skin-facing" herein) and "garment-facing" refer respectively to the relative location of an element or a surface of an element or group of elements. "Body-facing" implies the element or surface is nearer to the wearer during wear than another element of the same component. An example is the inner layer of the elastic laminate of the present invention wherein the inner layer (being an element of the elastic laminate) is nearer to the body of the wearer than the outer layer (being another element of the elastic laminate). "Garment-facing" implies the element or surface is more remote from the wearer during wear than another element of the same component. The garment-facing surface may face another (i.e. other than the wearable article) garment of the wearer, other items, such as the bedding, or the atmosphere.

"Proximal" refers to a portion being closer relative to the transverse centerline of the article, while "distal" refers to a portion being farther from the transverse centerline of the article.

"Film" refers to a sheet-like material wherein the length and width of the material far exceed the thickness of the material. Typically, films have a thickness of about 0.5 mm or less.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable".

"Hydrophilic" describes surfaces of substrates which are wettable by aqueous fluids (e.g., aqueous body fluids) deposited on these substrates. Hydrophilicity and wettability are typically defined in terms of contact angle and the strike-through time of the fluids, for example through a nonwoven fabric. This is discussed in detail in the American Chemical Society publication entitled "Contact Angle, Wettability and Adhesion", edited by Robert F. Gould (Copyright 1964). A surface of a substrate is said to be wetted by a fluid (i.e., hydrophilic) when either the contact angle between the fluid and the surface is less than 90°, or when the fluid tends to spread spontaneously across the surface of the substrate, both conditions are normally co-existing. Conversely, a substrate is considered to be "hydrophobic" if the contact angle is equal to or greater than 90° and the fluid does not spread spontaneously across the surface of the fiber. The contact angle test method used for the present invention is set out herein below.

"Extendibility" and "extensible" mean that the width or length of the component in a relaxed state can be extended or increased.

"Elasticated" and "elasticized" mean that a component comprises at least a portion made of elastic material.

"Elongation rate" means the state of elongation of a material from its relaxed, original length, namely an elongation rate of 10% means an elongation resulting in 110% of its relaxed, original length.

"Elongatable material", "extensible material", or "stretchable material" are used interchangeably and refer to a material that, upon application of a biasing force, can stretch to an elongation rate of at least 10% (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastic." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "non-elastic". For example, an elongatable material that has an initial length of 100 mm can extend at least to 150 mm, and upon removal of the force retracts to a length of at least 145 mm (i.e., exhibiting a 10% recovery).

As used herein, the term "nonwoven web" refers to a material which is a manufactured web/layer of directionally or randomly oriented fibers or filaments. The fibers may be of natural or man-made origin. Natural fibers may be selected from the group consisting of wheat straw fibers, rice straw fibers, flax fibers, bamboo fibers, cotton fibers, jute fibers, hemp fibers, sisal fibers, bagasse fibers, Hesper aloe fibers, miscanthus, marine or fresh water algae/seaweeds, silk fibers, wool fibers, and combinations thereof. Another group of fibers may also be regenerated cellulose fibers, such as viscose, Lyocell (Tencel®), rayon, modal, cellulose acetate fibers, acrylic fibers, cuprammonium rayon, regenerated protein fibers etc. Preferably, the natural fibers or modified natural fibers are selected from the group consisting of cotton fibers, bamboo fibers, viscose fibers or mixtures thereof. Preferably, the natural fibers are cotton fibers. Synthetic fibers may be selected from the group consisting of polyolefins (such as polyethylene, polypropylene or combinations and mixtures thereof), polyethylene terephthalate (PET), co PET, polylactic acid (PLA), polybutylene succinate (PBS), polyhydroxy alkanoid (PHA), nylon (or polyammide), or mixtures or combinations thereof. An alternative option is to use superabsorbent fibers, for example SAF™ which is a cross-linked terpolymer based on acrylic acid, which is partially neutralised to its sodium salt, commercially available from Technical Absorbents.

The fibers in a nonwoven web are consolidated by friction, and/or cohesion and/or adhesion, and/or by heat bonding, pressure bonding, heat and pressure bonding, and/or ultrasonic bond excluding paper and products which are woven, knitted, tufted, stitch-bonded. The fibers may be staple fibers (e.g. in carded nonwoven webs) or continuous fibers (e.g. in spunbonded or meltblown nonwoven webs).

Nonwoven webs can be formed by many processes such as meltblowing, spunlaying, solvent spinning, electrospinning, and carding, and the fibers can be consolidated, e.g., by hydroentanglement (in spunlaced nonwoven webs), air-through bonding (using hot air that is blown through the fiber layer in the thickness direction), needle-punching, one or more patterns of bonds and bond impressions created through localized compression and/or application of heat or ultrasonic energy, or a combination thereof. The fibers may, alternatively or in addition, be consolidated by use of a binder. The binder may be provided in the form of binder fibers (which are subsequently molten) or may be provided in liquid, such as a styrene butadiene binder. A liquid binder is provided to the fibers (e.g., by spraying, printing or foam application) and is subsequently cured to solidify.

The basis weight of nonwoven webs is usually expressed in grams per square meter (g/m$^2$).

In a spunlace nonwoven web the fibers have been carded as precursor web and then subjected to hydroentanglement to intermingle and intertwine the fibers with each other. Cohesion and the interlacing of the fibers with one another may be obtained by means of a plurality of jets of water under pressure passing through a moving fleece or cloth and, like needles, causing the fibers to intermingle with one another (hereinafter also referred to as "hydraulic interlacing"). Thus, consolidation of a spunlace nonwoven web is essentially a result of hydraulic interlacing. "Spunlace nonwoven web", as used herein, also relates to a nonwoven formed of two or more precursor webs, which are combined with each other by hydraulic interlacing.

The two or more webs, prior to being combined into one nonwoven by hydraulic interlacing, may have underdone bonding processes, such as heat and/or pressure bonding by using e.g., a patterned calendar roll and an anvil roll to impart a bonding pattern. However, the two or more webs are combined with each other solely by hydraulic interlacing. Alternatively, the spunlace nonwoven web is a single web, i.e. it is not formed of two or more precursor webs. Still in another alternative, the spunlace nonwoven web of the present invention may be formed of one precursor web onto which staple fibers are laid down. The staple fibers may not have been consolidated into a self-sustaining precursor web but the fibers are loosely laid onto the precursor web. The relatively loose staple fibers are then integrated and intertwined with each other and with the fibers of the underlying precursor web by (only) hydraulic interlacing. Spunlace nonwoven layers/webs can be made of staple fibers or continuous fibers (continuous fibers are also often referred to as filaments).

Through-air bonding (interchangeably used with the term "air-through bonding") means a process of bonding staple fibers or continuous fibers by forcing air through the nonwoven web, wherein the air is sufficiently hot to melt (or at least partly melt, or melt to a state where the fiber surface becomes sufficiently tacky) the polymer of a fiber or, if the fibers are multicomponent fibers, wherein the air is sufficiently hot to melt (or at least partly melt, or melt to a state where the fiber surface becomes sufficiently tacky) one of the polymers of which the fibers of the nonwoven web are made. The melting and re-solidification of the polymer provide the bonding between different fibers.

"Comprise," "comprising," and "comprises" are open ended terms, each specifies the presence of the feature that follows, e.g., a component, but does not preclude the presence of other features, e.g., elements, steps, components known in the art or disclosed herein. These terms based on the verb "comprise" encompasses the narrower terms "consisting essential of" which excludes any element, step or ingredient not mentioned which materially affect the way the feature performs its function, and the term "consisting" of which excludes any element, step, or ingredient not specified.

DETAILED DESCRIPTION OF THE INVENTION

Elastic Laminate of the Wearable Article

The elastic laminate comprised by the wearable article of the present invention comprises a first web and a second web being in a face to face relationship with each other. Each of the first and second web are comprised by the complete surface area of the elastic laminate. The first web and the second web are both nonwoven webs. The first web has a vertical wicking height after 60 seconds of less than 5 mm according to the test method set out herein below, and the second web is a nonwoven web having a vertical wicking height after 60 seconds of at least 5 mm according to the test method set out herein below.

The first web may have a vertical wicking height after 60 seconds which is at least 3 mm, or at least 4 mm, or at least 5, or at least 10 mm lower than the vertical wicking height after 60 seconds of the second web.

The first web having a vertical wicking height after 60 seconds of less than 5 mm, and the second web is a nonwoven web having a vertical wicking height after 60 seconds of at least 5 mm, as well as the first web having a vertical wicking height after 60 seconds being at least 3 mm, or at least 5 mm, or at least 8 mm, or at least 10 mm lower than the vertical wicking height of the second web is especially desirable when the elastic laminate is comprised by or forms an elastic belt of a wearable article, as is further described below.

At least 40%, or at least 50%, or at least 60%, or at least 70%, or at least 80% of the surface area of the elastic laminate, determined when the elastic laminate is stretched such that the first and/or second web are flattened out, may not comprise any further layer, such as further nonwoven webs, films, paper sheets or the like, except the first and second web. Further layers do, however, not exclude an extended portion of one of the first or second web which is folded over the elastic laminate at one of its edges to form an area of the elastic laminate which comprises either the first web sandwiched between the second web and the folded over, extended portion of the second web, or comprises the second web sandwiched between the first web and a folded over, extended portion of the first web. Such configurations are described in more detail below. Further layers also do not exclude portions of a central chassis, as explained in more detail below, attached to portions of the elastic laminate. Apart from these two embodiments, however, any other further layer may not be comprised in at least 40%, or at least 50%, or at least 60%, or at least 70%, or at least 80% of the surface area of the elastic laminate. Especially, at least 40%, or at least 50%, or at least 60%, or at least 70%, or at least 80% of the surface area of the elastic laminate may not comprise any layers sandwiched between the first and second web.

The first web may comprise at least 90 weight-% of synthetic fibers based on the total weight of the first web. The synthetic fibers may be selected from the group consisting of polyethylene, polypropylene, polyester, polylactic acid, and mixtures and combinations thereof.

The first web may be hydrophilic or hydrophobic. The second web may comprise at least 20 weight-%, or at least 30 weight-%, or at least 50 weight-%, or at least 60 weight-% of natural fibers based on the total weight of the second web. The natural fibers may be natural hydrophilic fibers. The natural hydrophilic fibers may, for example, be cotton, bamboo, viscose, cellulose, Lyocell, rayon, silk, or mixtures or combinations thereof.

The second web may further comprise synthetic fibers and the natural fibers and synthetic fibers may be mixed.

The vertical wicking height of the second web can be achieved via different combinations of natural fibers and/or fibers with higher surface area per volume and/or hydrophilicity. Examples of fibers with higher surface area/volume ratio can be thinner fibers, shaped fibers such as multilobal or Coolmax fibers, splittable fibers, natural fibers such as cotton fibers.

The second web may be formed of a first fibrous layer forming a first surface of the second web and a second fibrous layer forming a second surface of the second web. The fibers of the first fibrous layer may be synthetic fibers and the fibers of the second fibrous layer may be natural fibers. The first and second fibrous layer may be integrally combined with each other. At least a part of the natural fibers may interpenetrate the fibers of the first fibrous layer. The amount of natural fibers may gradually increase through the thickness from the first surface towards the second surface of the second web. The elastic laminate may not comprise any film layer or other web.

Consequently, natural fibers (or fibers with higher surface area), which are mostly present in the second fibrous layer of the second web, may also be present in the first fibrous layer of the second web and protrude out from the first surface the second web.

Integrally combining the first and second fibrous layer may, for example, be achieved by spunlacing, i.e., the second web may be a spunlace nonwoven web.

The first fibrous layer may be a preformed nonwoven, such as a spunbond nonwoven, which may be (point-) bonded with heat and/or pressure, e.g., by passing the layer between a pair of calendar rolls, one of which may have projections extending outwardly from the surface of the roll to impart a pattern of bonded areas on the spunbond layer; one or both of the calendar rolls may be heated). Alternatively, the preformed nonwoven forming the first fibrous layer may be a carded air-through bonded nonwoven. The second fibrous layer may be formed from staple fiber web which are laid onto the precursor nonwoven that forms the first fibrous layer.

Alternatively, though less preferred, the second fibrous layer may be a preformed nonwoven, such as the first fibrous layer described in the preceding paragraph.

The first and second fibrous layers may subsequently be combined by hydraulic interlacing.

If the first fibrous layer is a spunbond nonwoven precursor web, the web may be point bonded, by heat and/or pressure. In the bond points, the fibers of the first web may be fused together. The point bonds may be relatively small and the overall bonded area may be relatively small. Such nonwoven webs are considered to be better suitable for being integrally combined with the second fibrous layer, as the fibers of the second fibrous layer can more easily entangle and interpenetrate with the fibers of the first fibrous layer. If the overall bonded area and the individual point bonds are excessively large, the first fibrous layer may also rupture if the first and second fibrous layer are integrally combined by hydraulic interlacing.

In the elastic laminate, the second surface may face towards the first web and the first surface may face away from the first web.

The first web may form an inner web of the elastic laminate (especially if the elastic laminate is comprised by or forms an elastic belt of the wearable article) such that at least a portion first web is in direct contact with the skin of the wearer when the article is in use. The second web may form an outer web of the elastic laminate (especially if the elastic laminate is comprised by or forms an elastic belt of the wearable article). The outer web may form a part of an outermost surface of the wearable article, i.e. the surface which is facing towards the garment of the wearer in use. If the outer web comprises an extended portion which is folded over the inner web (as described in more detail below), this folded over, extended portion may contribute to the innermost surface of the wearable article.

If the elastic laminate is used as an elastic belt in a wearable article, the elastic laminate may form a front belt with a front waist edge and a back belt with a back waist edge. At the front and back waist edge, the elastic laminate may comprise the fold over region wherein the outer web is extended beyond the elastic laminate, and the extended portion of the outer web is folded over the inner web, such that a portion of the elastic belt comprises the inner web sandwiched between the outer web and the extended portion of the outer web. The extended folded over portion may have a longitudinal extension parallel with the longitudinal direction of the wearable article. For the front belt, the longitudinal extension of the extended folded over portion may have a dimension along the longitudinal direction of the wearable article which is less than 35%, or less than 30% of the longitudinal dimension of the front belt. For the back belt, the longitudinal extension of the extended folded over portion may have a dimension along the longitudinal direction of the wearable article which is less than 35%, or less than 30% of the longitudinal dimension of the back belt.

The total length of the side seams can be determined from the waist opening to the leg opening along a straight line along the side seams.

In addition, there is a growing desire to use natural fibers, such as cotton, silk, Lyocell, viscose and bamboo, in absorbent articles. Such use can contribute to improved sustainability of the article and is also considered healthier and more comfortable for the skin vs. synthetic fibers. However, while natural fibers readily absorb the fluid, such as a wearer's sweat, they do not easily transfer the liquid to other layers. Hence, nonwoven webs using natural fibers may potentially feel wet both on the skin of the wearer and on the surface facing the wearer's clothes. However, it has been found that by using natural fibers in a layer that forms the inside of an elastic laminate, the potential wet feel on the skin or from the outside can be eliminated.

In addition the presence of natural fibers, such as cotton or viscose, provides additional capacity for temporary storage of sweat until it is transported away via evaporation: in fact natural fibers, such as cotton and viscose, are known to be able to absorb moisture within the fiber itself at significantly higher levels than traditional synthetic fibers such as polypropylene or polyester. If desired this mechanism of increasing temporary sweat storage can be further enhanced via inclusion of superabsorbent fibers. The addition of natural fibers and/or superabsorbent fibers in the second fibrous layers allows to keep the moisture temporary in the middle of the elastic laminate, masking that moisture both on wearer skin surface and outer surface (i.e., garment-facing surface).

The first and second fibrous layer may be integrally combined with each other by spunlacing. The fibers of the second fibrous layer may be provided on a surface of the first fibrous layer and, subsequently, the fibers of the second fibrous layer may be intertwined with each other and with the fibers of the first fibrous layer by subjecting water jets onto the fibers of the second web (hydraulic interlacing). When providing the fibers of the first fibrous layer on the second fibrous layer, the fibers of the first fibrous layer may not have been previously consolidated. For example, synthetic fibers, such as polypropylene, may form a first fibrous layer (as a carded layer) of the second web and cotton fibers may form a second fibrous layer (also as a carded layer) of the second web. "Consolidated", as used herein, means that the fibers of a fibrous layer have not been bonded to each other, e.g. by providing a binder, by pressure, heat, or combinations thereof, and the fibers have also not been intertwined with each other by other means, such as by water jets (known as hydroentangling) or needle punching.

Vice versa, though less preferred, the first and second fibrous layer may be integrally combined with each other by spunlacing the fibers by providing the first fibrous layer on a surface of the second fibrous layer and, subsequently, the fibers of the first fibrous layer may be intertwined with the fibers of the second fibrous layer by subjecting water jets onto the fibers of the second web. When providing the fibers of the second fibrous layer on the first fibrous layer, the fibers of the second fibrous layer may not have been previously consolidated.

Alternatively to spunlacing, the fibers of the first and second fibrous layer may be integrally combined with each other by other known techniques, such as needle punching.

It is preferred that no adhesive (such as pressure sensitive adhesive or hot melt adhesive) and no binder is used to combine the first and the second fibrous layer.

The second fibrous layer may comprise natural hydrophilic fibers, modified natural hydrophilic fibers or combinations thereof. The second fibrous layer may be completely formed of such natural hydrophilic fibers, modified natural hydrophilic fibers or combinations thereof.

Alternatively, the second fibrous layer may comprise at least 20%, 25%, 50%, or at least 70%, or at least 90%, or at least 95%, by weight based on the total weight of the second fibrous layer, of natural hydrophilic fibers, modified natural hydrophilic fibers, hydrophilic synthetic fibers or combinations thereof. At least 25%, 50%, 70%, 90%, or at least 95% by weight based on the total weight of the second fibrous layer are hydrophilic fibers. Preferably, all fibers of the second fibrous layer are hydrophilic fibers.

All of the fibers of the first fibrous layer may be synthetic fibers, such as hydrophobic or hydrophilic synthetic fibers. Alternatively, synthetic fibers, such as hydrophobic synthetic fibers, may form at least 90%, or at least 95% by weight (based on the total weight of the first fibrous layer) of the first fibrous layer.

As the fibers of the first and second fibrous layer are integrally combined with each other (e.g. by spunlacing), the amount of natural hydrophilic fibers and/or modified natural hydrophilic fibers may gradually increases through the thickness of the second web from the first surface towards the second surface of the second web.

The natural hydrophilic fibers or modified natural hydrophilic fibers of the second fibrous layer may be selected from the group consisting of cotton, bamboo, viscose, cellulose, silk, or mixtures or combinations thereof. Preferred modified natural hydrophilic fibers are regenerated cellulose fibers. E.g., viscose is a modified natural hydrophilic fiber in that it is made of regenerated cellulose fibers such as cellulose fibers from wood or bamboo.

In the second web, the basis weight ratio of the first fibrous layer to second fibrous layer may be from 0.2 to 3, or from 0.5 to 2, or from 0.5 to 1.5, or from 0.5 to 1.

The first web may be an air-through bonded carded nonwoven web. Alternatively, the first web may be a spunbond web. If the first web is a spunbond web, the web may be (point-) bonded, by heat and/or pressure.

Elastic Laminate Used as a Belt for a Wearable Article

The elastic laminate may form the belt of a wearable article, such as a pant. The pant may be a disposable pant. A wearable article is described in more detail below. In an elastic laminate comprised by or forming the belt of a wearable article, the first web may form the inner web of the elastic laminate and the second web may form the outer web of the elastic laminate. At least a portion of the inner web will be in direct contact with the skin of the wearer when the article is applied on a wearer, i.e., it will form at least a portion of the innermost surface of the wearable article. The outer web may form at least a portion of the outermost surface of the wearable article, which will typically be in contact with the clothes of the wearer and which may frequently be touched by a caregiver.

The elastic laminate comprised by or forming an elastic belt of the wearable article comprises a first web and a second web being in a face to face relationship with each other. The first web and the second web are both nonwoven webs. The first web has a vertical wicking height after 60 seconds of less than 5 mm according to the test method set out herein below, and the second web is a nonwoven web having a vertical wicking height after 60 seconds of at least 5 mm according to the test method set out herein below.

The first web may have a vertical wicking height after 60 seconds which is at least 3 mm, or at least 4 mm, or at least 5, or at least 10 mm, or at least 15 mm lower than the vertical wicking height after 60 seconds of the second web.

The vertical wicking height of the first web and of the second web may not be more than 120 mm after 1 minute, or may not be more than 100 mm after 1 minute.

This configuration of the first and second web as well as their relation to each other with regard to vertical wicking height has been found to provide elastic laminates which can effectively transport sweat away from the wearer's skin. Sweat in the elastic laminate is transported from the first web (inner web) towards the second web (outer web). Once being in the second (outer) web, the sweat does not only get transported through the thickness of the second (outer) web towards the outside of the elastic laminate (i.e., through the garment-facing surface of the elastic laminate), but sweat can only be transported within the plane of the second (outer) web, thus being distributed over a wider area of the second (outer) web. Eventually, sweat distributed within the plane of the second web will also move to the outside of the elastic laminate.

As sweat may not form homogeneously on all areas of a wearer's skin, but more sweat may form locally on certain areas while less sweat may from in other regions covered by the wearable article, transportation of sweat within the plane of the second (outer) web can help to efficiently transport sweat away from the wearer.

On the other hand, having the first (inner) web of the elastic laminate with little or no vertical wicking ability, is beneficial as sweat is not or only to a small extent transported within the plane of the first (inner web). If larger amounts of sweat were transported within the plane of the first (inner) web, the sweat would remain in close contact with the wearer's skin, which may even result in larger areas of the wearer's skin being covered with sweat than as a direct result of sweating.

The first and second web may be directly joined with each other over an area of from about 5% to about 50%. By "directly joined" what is meant is that the first web and the second web are directly secured to each other by applying, for example, adhesive, ultrasound, pressure, heat, or combination thereof. The percentage of area of the first and second web that are directly joined with each other may vary depending on the joining method for forming the elastic laminate, as discussed in further detail below. The first and second web may be directly joined with each other over an area of from about 5% to about 50% to provide appropriate sweat management property, while also helping to maintain integrity as an elastic laminate. The area which is directly joined is determined relative to the overall area over which the first and second web are in contact with each other, either directly or via elastic strands that are provided between the first and second web (see more details below). The overall area is determined when the first and/or second web is laid out flat, e.g. by stretching the elastic strands, if present.

The second web (especially if forming the outer web) of the elastic laminate may have a plurality of openings at an Opening Rate of from about 5% to about 50% according to the measurements herein. By further provide a certain opening area for the second web, multiple moisture transport channels are provided which can contribute to an effective liquid removal and transport to the second web. The transport channels may be driven by capillary force gradient, and enhanced exposure to outside the elastic laminate away from the skin.

Also, to provide a thickness gradient, the basis weight of the first web may be not greater than the basis weight of the second web. The first web of the present invention is a nonwoven web which may have a basis weight of from about 5 g/m² to about 45 g/m², or from about 5 g/m² to about 35 g/m². The first and second web may have a fiber diameter of from 1 µm up to 35 µm. The first and/or second web may also comprise nanofibers having a fiber diameter of below 1 µm. Fiber diameter, as known in the industry, may also be expressed in denier per filament (dpf), which is grams/9,000 meters of length of fiber. In the second web, the fiber diameter of the second fibrous layer may be lower than the fiber diameter of the first fibrous layer and of the first web.

If the first web is the inner web, the first web may be made by processes such as spunbond, spunlace, carded or air-laid; and may comprise fibers and/or filaments made of polypropylene (PP), polyethylene (PE), polyethylene phthalate (PET), polylactic acid/polylactide (PLA) or conjugate fibers (such as PE/PET, PE/PP, PE/PLA) as well as natural fibers such as cotton or regenerated cellulosic fibers such as viscose or lyocell. If the inner web is the first web, the inner web may be made by biodegradable material, or derived from renewable resources. Non-limiting examples of materials suitable for the first web of the present invention include: 10 to 30 gsm spunbond nonwoven webs, or 12-30 gsm air-through carded nonwoven substrate made of PE/PET bi-component staple fiber, such as those available from Beijing Dayuan Nonwoven Fabric Co. Ltd. or Xiamen Yanj an New Material Co. Ltd., or a 8-30 gsm spun melt nonwoven substrate comprising PP monofilament or PE/PP bi-component fibers, such as those available from Fibertex or Fitesa.

If the first web is the inner web, the first web may preferably be relatively hydrophobic. The first (inner) web may be inherently hydrophobic, or the first web may be provided hydrophobicity by treating with hydrophobic melt additives into polymer resin in the fiber making process, or applying hydrophobic additives after the nonwoven is formed.

Hydrophobic additives may be fatty acids originated from vegetable, animal, and/or synthetic sources. Fatty acids may range from $C_8$-$C_{30}$ fatty acid, or from $C_{12}$-$C_{22}$ fatty acid, or substantially saturated fatty acid. Hydrophobic additives may be fatty acid derivatives including fatty alcohols, fatty acid esters, and fatty acid amides. Suitable fatty alcohols include those derived from $C_{12}$-$C_{30}$ fatty acids. Suitable fatty acid esters include those fatty acid esters derived from a mixture of $C_{12}$-$C_{30}$ fatty acids and short chain monohydric alcohols, preferably from a mixture of $C_{12}$-$C_{22}$ saturated fatty acids and short chain monohydric alcohols. The hydrophobic melt additive may comprise a mixture of mono, di, and/or tri-fatty acid esters. An example includes fatty acid ester with glycerol having at least one alkyl chain, at least two, or three chains to a glycerol, to form a mono, di, or triglyceride. Suitable triglycerides include glycerol thibehenate, glycerol tristearate, glycerol tripalmitate, and glycerol trimyristate, and mixtures thereof. Exemplary hydrophobic melt additives include glyceryl tristearate, such as those commercially available as Techmer PPM15000. Hydrophobic agents may be fatty acid amides including those derivatives from a mixture of C12-C28 fatty acids (saturated or unsaturated) and primary or secondary amines such as erucamide, oleamide and behanamide.

Exemplary hydrophobic additives which may be applied after the nonwoven is formed include surfactants and silicone-based finishes, natural oil or wax such as cotton seed oil, beeswax and shea butter.

The second web, if forming the outer web of the elastic laminate, may have a basis weight of from about 10 g/m² to about 45 g/m², or from about 10 g/m² to about 35 g/m², and may be adjusted such that the basis weight of the first web is greater, equal or smaller than the basis weight of the second web. If the second web is the outer web, the outer web may be made by processes such as spunbond, spunlace, carded or air-laid; and may comprise fibers and/or filaments made of polypropylene (PP), polyethylene (PE), polyethylene phthalate (PET), polylactic acid/polylactide (PLA) or conjugate fibers (such as PE/PET, PE/PP, PE/PLA) as well as natural fibers such as cotton or regenerated cellulosic fibers such as viscose or lyocell. Also, if the second web is the outer web, the second web may be made by biodegradable material, or derived from renewable resources.

The second web, if forming the outer web, may be hydrophobic or, preferably, may be hydrophilic.

Hydrophilic additives may be polypropylene and polyethylene polymers such as those available from Techmer PM (Clinton, TN, US) sold under the trade name of Techmer PPM15560; TPM12713, PPM19913, PPM 19441, PPM19914, and PM19668. Hydrophilic additives may include, ionic surfactants, cationic surfactants, amphoteric surfactants or mixtures thereof. Exemplary hydrophilic additives include 100410 AF PE MB marketed by Ampacet, Irgasuf HL560 commercially available from Ciba Speciality Chemicals Inc., Hydrosorb 1001 commercially available from Goulston Technologies Inc., Cirrasol PP682 commercially available from Uniqema, Stantex S 6327 commercially available from Cognis, Silastol PST, Silastol PHP26 commercially available from Schill & Seilacher, Silwet L-7608 commercially available from Momentive Performance Materials, silicone surfactant with a polyethylene oxide chain and molecular weight above 700 g/mol by the name Polyvel S-1416 or VW 315 commercially available from Polyvel Inc.

If the second web is the outer web, exemplary material for the second web include: air-through carded nonwoven having a thickness of at least about 50 μm, or at least about 80 μm, or at least about 200 μm. The thickness may be less than 2000 μm, or less than 1500 μm, or less than 1250 μm. Such material may provide a soft lofty feeling to the garment-facing web. If the second web is the outer web, suitable for the outer web of the present invention are air-through carded nonwoven material made of co-centric bicomponent fiber, crimping fiber made through core eccentric bicomponent filament or side by side bicomponent filament. Non-limiting examples of materials suitable for the outer web include: 12 g/m² to 45 g/m² air-through carded nonwoven substrate comprising PE/PET bi-component fibers, such as those available from Beijing Dayuan Nonwoven Fabric Co. Ltd. or Xiamen Yanjan New Material Co. Ltd., and 8-45 gsm spun melt nonwoven substrate comprising PP monofilament or PE/PP bi-component fibers, such as those available from Fibertex or Fitesa.

The basis weight and material thickness of the first and second web herein is related to materials obtained from a finished product according to the "Preparation for Thickness and Basis Weight" below and measured by "Base caliper method—ASTM D 654 Standard Test Method for Thickness of Paper and Paper Board" with modification of the loading to 500 Pa, and by "Basis weight—ASTM D 756 Practice for Determination of Weight and Shape Changes of Plastics Under Accelerated Service Conditions", respectively.

The second web, if forming the outer web may have a plurality of openings at an Opening Rate of from about 5% to about 50%, or from about 5% to about 30%, or from about 7% to about 15%, or from about 9% to about 25%, and an Effective Opening Area of from about 0.1 mm² to about 25 mm², or from about 0.4 mm² to about 2.0 mm², of from about 1.0 mm² to about 5 mm², or from about 4.0 mm² to about 8 mm², or from about 7 mm² to about 15 mm², according to the measurements herein.

Alternatively, or in addition, the first web, if forming the inner web may have a plurality of openings at an Opening Rate of from about 5% to about 50%, or from about 5% to about 30%, or from about 7% to about 15%, or from about 9% to about 25%, and an Effective Opening Area of from about 0.1 mm² to about 25 mm², or from about 0.1 mm² to about 10 mm², or from about 0.4 mm² to about 2.0 mm², or from about 0.5 mm² to about 4 mm², of from about 1.0 mm² to about 5 mm², or from about 4.0 mm² to about 8 mm², or from about 7 mm² to about 15 mm², according to the measurements herein For the first web and/or the second web, the openings may be apertures, slits, or the like. Preferably, the openings are apertures. If the first and second web each have openings, the openings of the first web may be congruent with the openings of the second web. Alternatively, the first and second web each have openings, the openings of the first web may not be congruent with the openings of the second web. In a still further alternative, if the first and second web each have openings, some of the openings in the first web may be congruent with all or some the openings in the second web, while the remaining openings in the first web may not be congruent with the openings of the second web and the second web may also have opening which are not congruent with the some of the opening of the first web.

The openings in the first and/or second web may be apertures having an aspect ratio of less than about 5. The aspect ratio of an opening is determined as such. The greatest dimension of the opening is measured, wherein the direction of the greatest dimension defines the first axis. The line perpendicular to the first axis is defines the second axis. The dimension of the opening along the second axis is measured and defined the cross dimension. The aspect ratio is the greatest dimension divided by the cross dimension.

The openings may be made by female-male hot pin process, hole punching process, hydroentanglement process using water jets and a screen to create holes, and combinations thereof. The openings may be made by creating a plurality of weakened locations by heat or pressure followed by incrementally stretching, causing said nonwoven web to rupture at the weakened locations such as described in U.S. Pat. No. 5,628,097. Such rupturing method may be particularly useful for nonwovens using spunbonded fibers and meltblown fibers. The openings may be three-dimensional, nonhomogeneous, unaligned and forming a pattern as described in PCT Publication WO 2016/73712.

In a preferred embodiment, the second web, if forming the outer web, has a plurality of openings while the first web, if forming the inner web, may or may not have openings.

The first web or the second web may be devoid of openings (alternatively, both layers may be devoid of openings). Namely, the combination of the first and second web may provide a Relative Opening Rate of 100%, less than 100%, or less than about 50%, or less than about 15% according to the measurements herein. What is meant by Relative Opening Rate is the percentage of opening of the elastic laminate which matches the opening of the second web. When there is only opening in the second web, the Relative Opening Rate is 0%, while when the openings of the second web and the first web completely match, the Relative Opening Rate is 100%. In the present invention, the first web may optionally have openings, and when so, the pattern and density of the openings may be changed so as to completely or partially match with those of the second web.

The first web and the second web may be directly joined to each other over an area of from about 5% to about 50% by any means known in the art, such as by applying, ultrasound, pressure, or heat, for providing the elastic laminate of the present invention. The first and second web may be at least partially directly joined by adhesive. When adhesive is used for joining the first and second webs, the area in which adhesive is applied between the first and second webs is considered as area in which the webs are directly joined. When using adhesive as a joining means, the adhesive agent may be applied intermittently, such as in spiral pattern. Alternatively or additionally, the adhesive may be applied by a slot coat pattern for sake of better process control, wherein the area in which adhesive is applied is from about 5% to about 50%, or from about 5% to about 40%, or from about 5% to about 30% of the laminate planar area. Alternatively or additionally, the first and second web may be at least partially directly joined by means which directly join the fibers of the first and second webs, such as by heat, pressure, or ultrasound.

The elastic laminate of the present invention may have an elongation rate of at least about 110% in at least one direction. Elasticity may be imparted by laminating an elastic body between the first and second web. The elastic body may preferably be a plurality of elastic strands, but may alternatively though less preferred, be an elastic sheet. The webs and elastic bodies may be at least partially joined by means selected from the group consisting of; adhesive, heat, pressure, ultrasound, and combinations thereof. Referring to FIG. 1B, adhesive may be applied for joining the elastic bodies to the first and/or second web, and further applied via a slot coat in a pattern of panel adhesive agents 233 for joining the first and second web. Alternatively or additionally, the elastic bodies may be joined by deforming the first and/or second web contacting the elastic body via ultrasound or heat, to anchor the elastic body against the first and/or second web. Though less preferred, the elastic body may be an elastic sheet; wherein ultrasound is applied at a certain energy level to the first web, second web, and elastic sheet, combined, such that the fibers of the first web and the second web come into direct contact with each other. These directly joined areas of fibers are also considered as area in which the first and second webs are directly joined. The first and second web may be non-elastic.

Elastic laminates obtained by any of the aforementioned joining methods need not be embossed, or mechanically activated, beyond the force needed to at least partially directly join the webs. Thus, the elastic laminate may be economically made. The directly joined area may be measured by stretching the elastic laminate to an uncontracted condition, for example with a force of 25N, and observing the planar area where the first and second layers are directly joined.

The Wearable Article

The present invention relates to a wearable article comprising an elastic laminate. The elastic laminate may form at least a part of a wearable article that is in direct contact with the skin.

If used as an elastic belt for a wearable article, the elastic laminate comprises an inner web and an outer web. The inner web is closer to the wearer than the outer web when the article is worn. The inner web may be in direct contact with the skin of the wearer when the article is worn. The outer web may form at least a part of the outer surface of the wearable article.

Generally, the elastic laminate may be used as a component selected from the group consisting of elastic belts, waistbands, side panels, leg cuffs, and outer covers, of the wearable article.

The present elastic laminate is particularly useful as an elastic belt. The wearable article may be a pant. An exemplary pant is described in PCT Publication WO 2006/17718A. The pant may comprise a central chassis 38 to cover the crotch region of the wearer when the article is worn, a front belt 84 and a back belt 86 (hereinafter may be referred to as "front and back belts") comprising the elastic laminate of the present invention, the front and back belts 84, 86 forming a discrete ring-like elastic belt 40 (hereinafter may be referred to as "waist belt") extending transversely defining the waist opening. The wearable article 20 may be a uni-body type pant wherein the central chassis 38 is continuous with the front and back belt 84, 86, wherein the leg openings are continuously formed (not shown). The belt-type pant may be advantageous in that the central chassis 38 has better breathability, thus providing better sweat management for the entire wearable article.

For the elastic laminate of the present invention, the first web is the inner web and the second web is the outer web of the elastic belt.

Figure 1B:
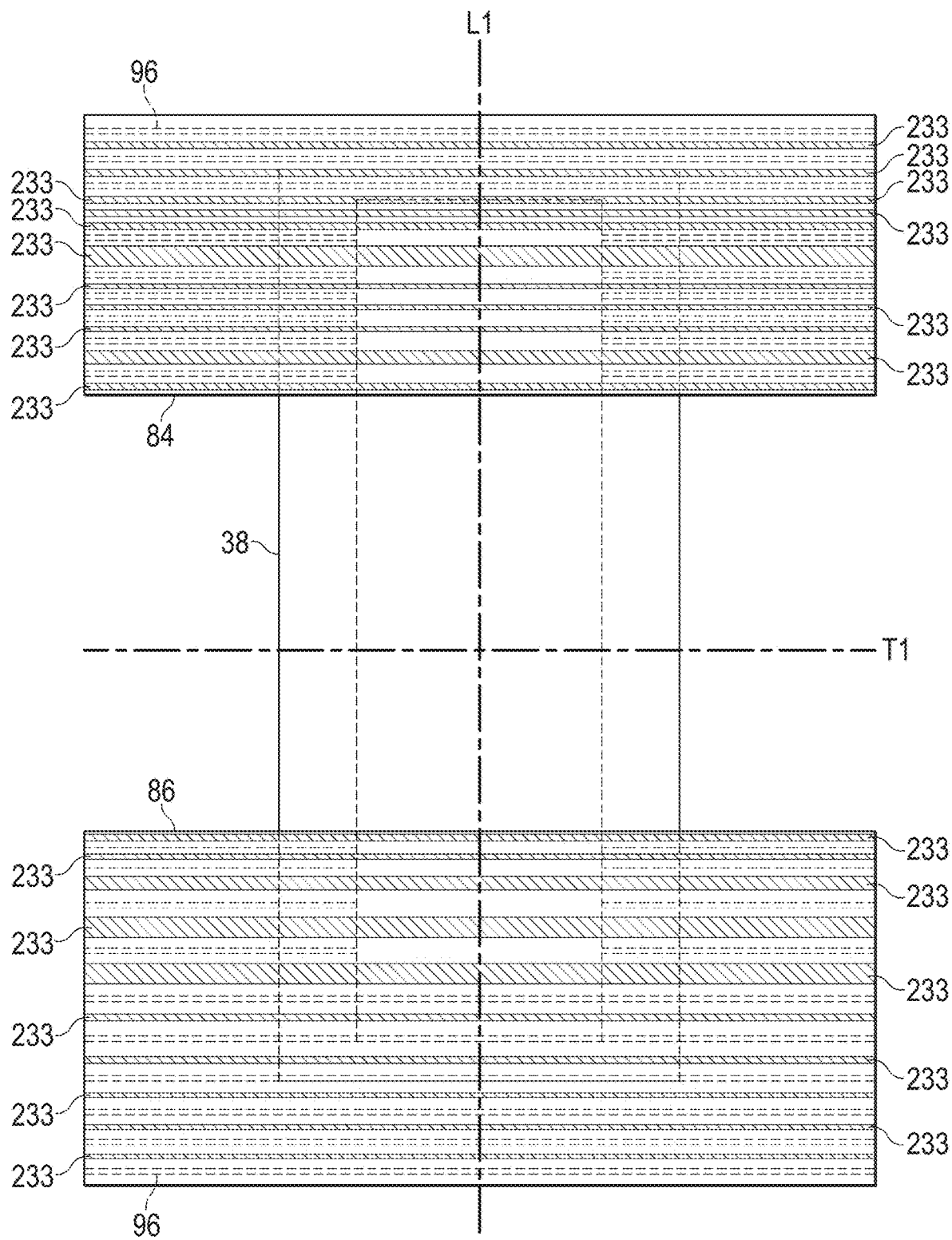

FIG. 1A is a perspective view of an example for a wearable article of the present invention of the pant with the seams un-joined and in its flat uncontracted condition showing the garment-facing surface. The wearable article has a longitudinal centerline L1 which also serves as the longitudinal axis, and a transverse centerline T1 which also serves as the transverse axis. The wearable article has a body facing surface, a garment facing surface, a front region 26, a back region 28, a crotch region 30, and seams which join the front region 26 and the back region 28 to form two leg openings and a waist opening. As each of the first and second web are comprised by the complete surface area of the elastic laminate, the seams also comprise the first and second web of both, the front belt 84 and the back belt 86. At least a portion of or the entirety of the front belt 84, or at least a portion of or the entirety of the back belt 86, or the entire discrete ring-like elastic belt 40 may be made by the elastic laminate of the present invention. The front and back belts 84, 86 and the central chassis 38 jointly define the leg openings.

Figure 2A:
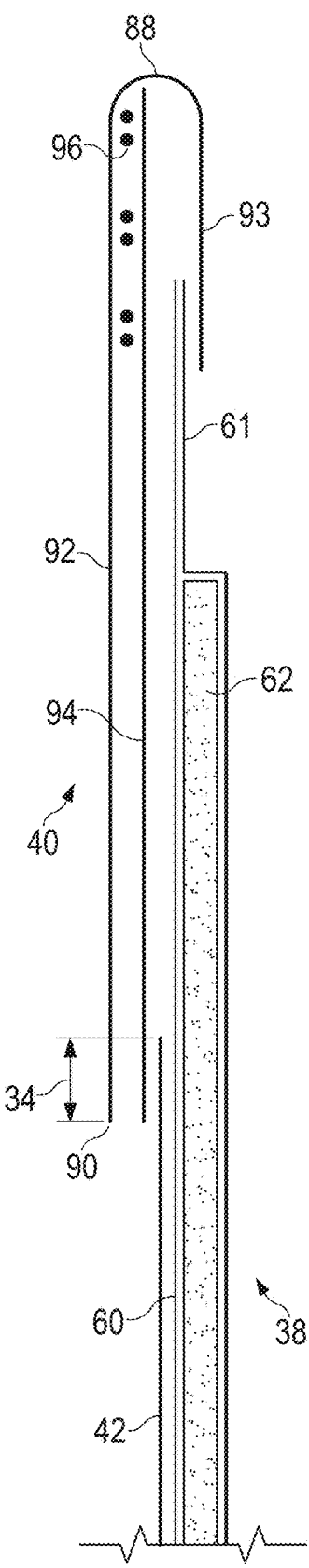
FIGS. 2A-2C are schematic cross section views of embodiments of wearable articles of the present invention
Figure 2B:
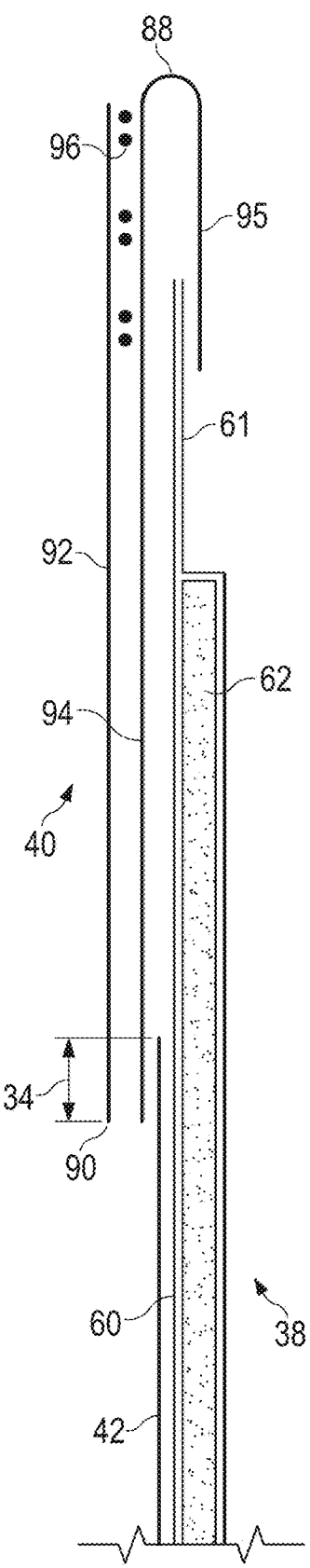
Figure 2C:
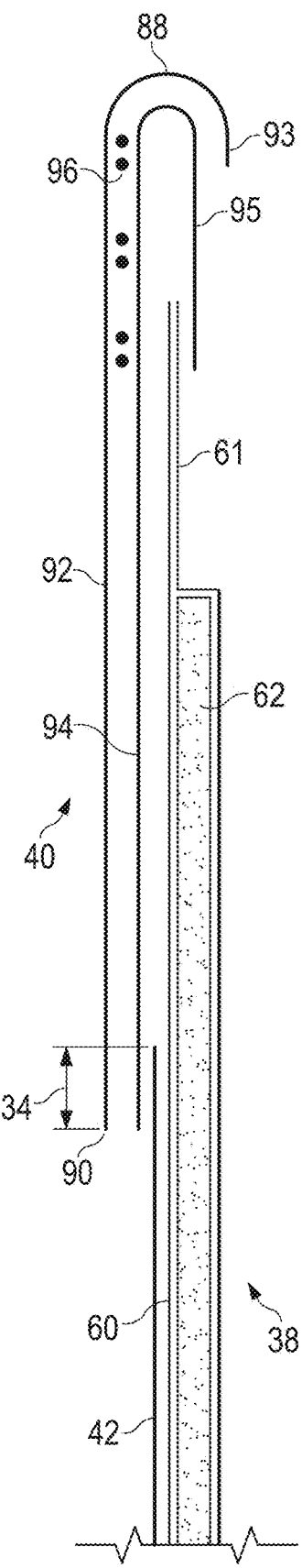
Figure 3:
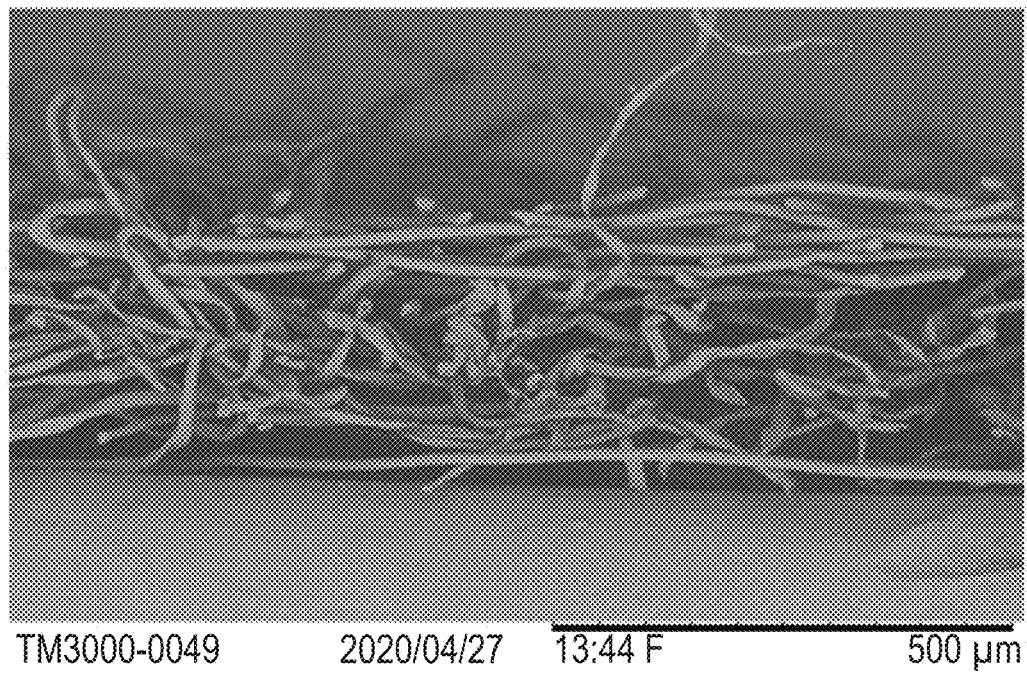
FIG. 3 shows a SEM photography of a second web with first and second fibrous layer, wherein the upper side is the first fibrous layer (polypropylene fibers) and the bottom side is the second fibrous layer (cotton fibers). The SEM photography shows fibers of the second fibrous layer interpenetrating the fibers of the first fibrous layer. It can also be seen that some fibers of the second fibrous layer penetrate through the first fibrous layer and outside of the first surface.

As exemplarily shown in FIGS. 2A and 2A-2C, the central chassis 38 may comprise a backsheet 60 and an outer cover layer 42 for covering the outer side of the backsheet 60. The backsheet 60 may be a water impermeable film. At least a portion of or the entirety of the outer cover layer 42 may be the elastic laminate of the present invention. The central chassis 38 may contain an absorbent core 62 for absorbing and containing body exudates disposed on the central chassis 38. As exemplified in in FIG. 1A, the central chassis 38 may have a generally rectangular shape, left and right longitudinally extending side edges 48 (hereinafter may be referred to as "side edge") and front and back transversely extending end edges 50 (hereinafter may be referred to as "end edge"). The central chassis 38 also has a front waist panel 52 positioned in the front region 26 of the wearable article, a back waist panel 54 positioned in the back region 28, and a crotch panel 56 between the front and back waist panels 52, 54 in the crotch region 30. The center of the front belt 84 is joined to a front waist panel 52 of the central chassis 38, the center of the back belt 86 is joined to a back waist panel 54 of the central chassis 38, the front and back belts 84, 86 each having a left side panel and a right side panel 82 where the central chassis 38 does not overlap. The central chassis 38 may comprise one or more leg cuffs per side for gasketing the leg opening. At least a portion of, or at least one of, or all of, the leg cuffs may be the elastic laminate of the present invention.

While not depicted, the wearable article of the present invention may be a taped diaper having a longitudinal axis, a transverse axis, a body facing surface, and a garment facing surface. The wearable article may have a central chassis comprising a front region, a back region, and a crotch region, each defined by a laterally extending line notionally divided along the longitudinal axis in 3 equal lengths. The front region and/or the back region may be provided with fastening members for fastening the article to configure the waist opening and leg openings. The waist opening may comprise a waistband. The fastening member may be made by a connecting part connecting to the central chassis, a stretchable side panel which is stretchable in the lateral direction, and an engaging part having engaging elements such as hooks. The front region and/or the back region may be provided with a landing zone for receiving the engaging elements of the fastening member. The landing zone may be loops engageable with the hooks. At least a portion of, or the entirety of, the waistband, side panels, or landing zones of the wearable article may be the elastic laminate of the present invention.

The ring-like elastic belt 40 of the pant of the present invention acts to dynamically create fitment forces and to distribute the forces dynamically generated during wear. The proximal edge 90 is located closer than the distal edge 88 relative to the crotch panel 56 of the central chassis 38. The front and back belts 84, 86 may be joined with each other only at the side edges 89 at the seams to form a wearable article having a waist opening and two leg openings. Each leg opening may be provided with elasticity around the perimeter of the leg opening. For the belt-type pant, the elasticity around the leg opening may be provided by the combination of elasticity from the front belt 84, the back belt 86, and any from the central chassis 38.

The front belt 84 and back belt 86 of the pant are configured to impart elasticity to the belt 40. The front belt 84 and the back belt 86 may each be formed by the present elastic laminate comprising a plurality of elastic bodies 96, such as elastic strands, running in the transverse direction, an inner web 94 (=the first web of the elastic laminate), and an outer web 92 (=the second web of the elastic laminate). Optionally an outer sheet fold over 93 which is an extended portion of the outer web (=second web) may be formed by folding the extended portion of the outer web. Alternatively, though less preferred, an inner sheet fold over 95 may be formed, which is an extension of the inner sheet material may be formed by folding the inner sheet material. The outer web 92 may be made of the same nonwoven substrate of the present invention as the outer cover layer 42 to provide integral aesthetic and tactile senses for the article. The outer web fold over is preferably provided around the waist opening 88 of the wearable article.

When the central chassis 38 contains an absorbent core, some or all of the areas of the front or back belt 84, 86 overlapping the absorbent core may be made devoid of elasticity. Referring to FIG. 1A, areas of the front waist panel 52 and back waist panel 54 in which the elastic bodies 96 are deactivated are shown in blank. For example, as seen in the back belt 86, the elastic bodies 96 overlapping the absorbent material non-existing region 61 and toward the distal edges of the absorbent core 62 may be disposed in active elasticity for good fit of the central chassis 38. This may be advantageous in preventing leakage.

Providing the folded over, extended portion 93 of the outer web (=second web) is advantageous for avoiding the waist opening 88 ending in sharp edges of the front or back belt 84, 86. Further, any elastic bodies 96 in the front or back belt 84, 85 may be disposed at least about 2 mm away, or from about 5 mm to about 9 mm away from the waist opening, to avoid the waist opening to be sharp, and also to ensure that any elastic body is not accidentally exposed during manufacture or use. The folded over, extended portion 95, 93 of the outer web (=second web) may extend toward the proximal edge of the belt such that there is overlap between the central chassis 38 by at least about 10 mm, or by at least about 15 mm, to secure integrity between the front and or back belt 84, 86 and central chassis 38.

Referring to FIG. 2A, the front belt 84 and/or back belt 86 may comprise folded over, extended portion 95, 93 of the outer web (=second web) wherein the outer web comprises an extended portion extending beyond the distal edge 88 of the belt (i.e. the distal edge 88 forming the front or back waist edge, respectively) and being folded over the distal edge of the first web such that at least a portion of the elastic belt comprises one layer of the inner web (=first web) sandwiched between two layers of the outer web (one of these layers being the extended portion).

Referring to FIG. 1A, the transverse width LW of the back belt 86 in the uncontracted condition may be the same as the transverse width of the front belt 84 of the same condition. Such an article may be economically made. The longitudinal length LB of the back belt 86 between the back distal edge 88 and the back proximal edge 90 along its entire width LW of the back belt 86 may be approximately the same as the longitudinal length LF of the front belt 84 between the front distal edge 88 and the front proximal edge 90. In such configuration, the seams close the front and back belt 84, 86 side edges 89 of the same length for forming the article. Such an article may be economically made. The back belt 86 may have a greater longitudinal length LB between the back distal edge 88 and the back proximal edge 90 along its entire width LW of the back belt 86 in the transverse direction than the longitudinal length LF of the front belt 84 between the front distal edge 88 and the front proximal edge 90. In such configuration, when the wearable article is assembled to form the waist opening and the leg openings, the wearable article is folded along the transverse centerline T1 such that the front distal edge 88 is aligned with the back distal edge 88. The front side edge 89 is also aligned with a portion of the back side edge 89. Then the front belt 84 and the back belt 86 are joined at the front and back side edges 89 at the seams. The front and back proximal edges 90, however, may not be aligned to one another. The back proximal edge 90 may be disposed longitudinally closer than the front proximal edge 90 relative to the transverse center line T1 such that the proximal portion of the back side panel 82 extends toward the crotch panel 56 of the central chassis 38 beyond the front proximal edge 90. The side edge of the proximal portion of the back side panel 82 may not be joined to anywhere and free from attachment. Thus, the proximal portion of the back side panel 82 provides a buttock cover.

For the front belt 84, the longitudinal extension of the extended folded over portion 93 of the outer web may have a dimension along the longitudinal direction of the wearable article which is less than 35%, or less than 30%, of the longitudinal dimension LF of the front belt. For the back belt 86, the longitudinal extension of the extended folded over portion 93 may have a dimension along the longitudinal direction of the wearable article which is less than 35%, or less than 30% of the longitudinal dimension LB of the back belt.

Referring to FIGS. 1A and 2A-2C, the front and back belts 84, 86 may be discontinuous with one another in the crotch region 30, such that the outer cover layer 42 is the garment-facing surface in the crotch region 30. The outer cover layer 42 may extend only partly in the longitudinal direction of the front waist panel 52 and the back waist panel 54 to leave the distal parts of the front waist panel 52 and the back waist panel 54 free of the outer cover layer 42. Namely, the longitudinal length of the outer cover layer 42 may be longer than the longitudinal length of the crotch panel 56 and shorter than the longitudinal length of the backsheet 60. By such configuration, the distal parts of the front waist panel 52 and the back waist panel 54 are devoid of the outer cover layer 42, providing better breathability and sweat management for the elastic belt 40. Further, this may provide cost saving of the outer cover layer 42 material. Accordingly, looking at the layers of elements between the garment facing surface and the backsheet 60 of the center chassis 38, there exists a transitional region 34 disposed on the front and back waist panel 52, 54 where the outer cover layer 42 is present. The longitudinal length of the transitional region 34 may be made as short as possible, for example, less than about 20 mm, or less than about 15 mm, or less than about 10 mm. Further, adhesive may be applied on the entire area of the transitional region 34, or the entire area leaving no more than up to 5 mm, in the longitudinal direction, from the distal edge of the transitional region 34. For providing attractive artwork for a wearable article in an economical manner, printing may be provided on the garment facing side of the backsheet 60. By providing the transitional region 34 as short as possible, applying adhesive to the transitional region 34 to enhance transparency, or simply avoiding displaying artwork in the transitional region 34, compromised appearance of the artwork over different layers of material between the artwork and the observer may be avoided. Referring to FIG. 1A, artwork on the backsheet 60 may be printed in regions 40F and/or 40B.

The articles of the present invention provide improved sweat management properties, are easy to apply and comfortable to wear, while being economic to make.

Bio-Based Materials

The elastic laminate may comprise a bio-based content value from about 10% to about 100% using ASTM D6866-10, method B, or from about 25% to about 75%, or from about 50% to about 60%.

The first web, the first fibrous layer and/or the second fibrous layer of the elastic laminate may comprise a bio-based content value from about 10% to about 100% using ASTM D6866-10, method B, or from about 25% to about 75%, or from about 50% to about 60%.

In order to apply the methodology of ASTM D6866-10 to determine the bio-based content of a single component material (i.e., the elastic laminate), that material is isolated and cleaned such that the resulting specimen reflects the constituent starting material as closely as possible. For example, if a nonwoven component of an elastic nonwoven laminate is of interest, the laminate is deconstructed (with elastic strands removed) and the nonwoven layer is washed with an appropriate solvent so as to remove any residual adhesive present. In order to apply the methodology of ASTM D6866-10 to an sample assembly of two or more materials of differing or unknown compositions, the sample is homogenized by grinding the material into particulate form (with particle size of about 20 mesh or smaller) using known grinding methods (such as with a Wiley grinding mill). A representative specimen of suitable mass is then taken from the resulting sample of randomly mixed particles.

Validation of Polymers Derived from Renewable Resources

A suitable validation technique is through 14C analysis. A small amount of the carbon dioxide in the atmosphere is radioactive. This 14C carbon dioxide is created when nitrogen is struck by an ultra-violet light produced neutron, causing the nitrogen to lose a proton and form carbon of molecular weight 14 which is immediately oxidized to carbon dioxide. This radioactive isotope represents a small but measurable fraction of atmospheric carbon. Atmospheric carbon dioxide is cycled by green plants to make organic molecules during photosynthesis. The cycle is completed when the green plants or other forms of life metabolize the organic molecules, thereby producing carbon dioxide which is released back to the atmosphere. Virtually all forms of life on Earth depend on this green plant production of organic molecules to grow and reproduce. Therefore, the 14C that exists in the atmosphere becomes part of all life forms, and their biological products. In contrast, fossil fuel based carbon does not have the signature radiocarbon ratio of atmospheric carbon dioxide.

Assessment of the renewably based carbon in a material can be performed through standard test methods. Using radiocarbon and isotope ratio mass spectrometry analysis, the bio-based content of materials can be determined. ASTM International, formally known as the American Society for Testing and Materials, has established a standard method for assessing the bio-based content of materials. The ASTM method is designated ASTM D6866-10.

The application of ASTM D6866-10 to derive a "bio-based content" is built on the same concepts as radiocarbon dating, but without use of the age equations. The analysis is performed by deriving a ratio of the amount of organic radiocarbon (14C) in an unknown sample to that of a modern reference standard. The ratio is reported as a percentage with the units "pMC" (percent modern carbon).

The modern reference standard used in radiocarbon dating is a NIST (National Institute of Standards and Technology) standard with a known radiocarbon content equivalent approximately to the year AD 1950. AD 1950 was chosen since it represented a time prior to thermo-nuclear weapons testing which introduced large amounts of excess radiocarbon into the atmosphere with each explosion (termed "bomb carbon"). The AD 1950 reference represents 100 pMC.

"Bomb carbon" in the atmosphere reached almost twice normal levels in 1963 at the peak of testing and prior to the treaty halting the testing. Its distribution within the atmosphere has been approximated since its appearance, showing values that are greater than 100 pMC for plants and animals living since AD 1950. It's gradually decreased over time with today's value being near 107.5 pMC. This means that a fresh biomass material such as corn could give a radiocarbon signature near 107.5 pMC.

Combining fossil carbon with present day carbon into a material will result in a dilution of the present day pMC content. By presuming 107.5 pMC represents present day biomass materials and 0 pMC represents petroleum derivatives, the measured pMC value for that material will reflect the proportions of the two component types. A material derived 100% from present day soybeans would give a radiocarbon signature near 107.5 pMC. If that material was diluted with 50% petroleum derivatives, for example, it would give a radiocarbon signature near 54 pMC (assuming the petroleum derivatives have the same percentage of carbon as the soybeans).

A biomass content result is derived by assigning 100% equal to 107.5 pMC and 0% equal to 0 pMC. In this regard, a sample measuring 99 pMC will give an equivalent bio-based content value of 92%.

Assessment of the materials described herein can be done in accordance with ASTM D6866. The mean values quoted in this report encompasses an absolute range of 6% (plus and minus 3% on either side of the bio-based content value) to account for variations in end-component radiocarbon signatures. It is presumed that all materials are present day or fossil in origin and that the desired result is the amount of biobased component "present" in the material, not the amount of biobased material "used" in the manufacturing process.

Test Methods

Vertical Wicking Height Method

The Vertical Wicking Height Method is used to determine the Vertical Wicking Height of a web available as roll-stock raw material or a web removed from the elastic laminate of an article. The method is performed according to the general principles described in EDANA method 10.4 (02), section 6 "LIQUID WICKING RATE". Five test pieces, having dimensions of 250 mm in length and 25 mm in width, are tested.

If the web is available as roll stock, a specimen having a width of 25±1 mm and a length of 250±1 mm, wherein the length is measured parallel to the machine direction of the material.

If the web is not available as roll stock, it is removed from an article. To remove the elastic laminate from the article the following procedure is used. It is identified the elastic laminate of the wearable article and cut a piece of elastic laminate, having a width of 25±1 mm and a length of 250±1 mm, wherein the length is referred to the state of the elastic laminate stretched until the material is flat, i.e., the laminate shows no wrinkles. The long direction of the specimen is parallel to the lateral axis of the product. If needed, the elastic laminate is separated from other components of the wearable article via applying a cryogenic freeze spray without damaging the material properties. Once the elastic laminate is removed, the first web and second web are carefully separated without permanently altering the properties of the first and second web. Four additional like specimens from like absorbent articles are prepared for a total of five specimens. At the end of this sample preparation procedure, five like specimens of the first web and five like specimens of the second web result.

The web specimens are conditioned for 24 h at 23° C. and 50% relative humidity. Each specimen is conditioned for 24 h at 23° C. and 50% relative humidity and then analyzed Each analysis is carried at 23° C. and 50% relative humidity. The fluid used is 0.9% (mass per mass) NaCl water solution.

Each specimen is hung vertically with the bottom punctured by two stainless steel needles and attached to an additional clamp (30±1 g) to keep the sample extended. The two needles are inserted in the nonwoven within the bottom 15 mm of the length of the nonwoven. The two needles are inserted parallel to the direction of the 25 mm width of the specimen, with a distance of about 8 mm in between the two needles. The clamp is clamped in between two needles. The stainless steel needle is at least as wide as the strip and has a diameter sufficient to prevent the clamp from sliding over the needle. The clamp is 25 mm wide.

The bottom of the specimen is dipped into the fluid reservoir at beginning, and the vertical wicking height is measured at time points of interest from the point at which the web intersects the free liquid surface. Each specimen is measured in this way, and for each specimen, the height of capillary rise of liquid at 10 s, 30 s, and 60 s is recorded the nearest 1 mm. If the capillary rise is not a uniform straight line, the highest distance, farthest from the free liquid surface, is measured.

The arithmetic means of the capillary rise among the five specimens of the first web corresponding to each of 10 sec, 30 sec and 60 sec are calculated and are reported as the First Web Vertical Wicking Height after 10 sec, First Web Vertical Wicking Height after 30 sec, and First Web Vertical Wicking Height after 60 sec, respectively, to the nearest 1 mm. The arithmetic means of the capillary rise among the five specimens of the second web corresponding to each of 10 sec, 30 sec and 60 sec are calculated and are reported as the Second Web Vertical Wicking Height after 10 sec, Second Web Vertical Wicking Height after 30 sec, and Second Web Vertical Wicking Height after 60 sec, respectively, to the nearest 1 mm Contact Angle Test Method A rectangular specimen of the web, measuring 1 cm×2 cm, is removed from the elastic laminate of a wearable article so as not to disturb the structure of the material. The specimen has a length of (2 cm) aligned parallel to the longitudinal centerline of the article. The specimen of interest may be separated from the other components of the wearable article such as the inner web or the outer web of the elastic laminate, elastic bodies between the inner and outer web, or backsheet or any other material by techniques such as applying freeze spray, or other suitable methods that do not permanently alter the properties of the web. The extracted web specimen is conditioned at a temperature of 23±2° C. and a relative humidity of 50±10% for at least 24 hours. The specimen is handled gently throughout by the edges using forceps and is mounted flat on an SEM specimen holder using double-sided tape. Multiple specimens are prepared in similar fashion as needed to accumulate the requisite number of individual measurements.

The specimen is sprayed with a fine mist of water droplets generated using a small hobby air-brush apparatus. The water used to generate the droplets is distilled deionized water with a resistivity of at least 18 Me-cm. The airbrush is adjusted so that the droplets each have a volume of about 2 pL. Approximately 0.5 mg of water droplets are evenly and gently deposited onto the specimen Immediately after applying the water droplets, the mounted specimen is frozen by plunging it into liquid nitrogen. After freezing, the sample is transferred to a Cryo-SEM prep chamber at −150° C., coated with Au/Pd for 2 minutes, and transferred into Cryo-SEM chamber at −150° C. A Gatan Alto 2500 Cryo-SEM prep chamber or equivalent instrument is used as preparation chamber. A Hitachi S-4700 Cryo-SEM or equivalent instrument is used to obtain high-resolution images of the droplets on the fibers. Droplets are randomly selected, though a droplet is suitable to be imaged only if it is oriented in the microscope such that the projection of the droplet extending from the fiber surface is approximately maximized. The contact angle between the droplet and the fiber is determined directly from the image.

The above procedure is used on the first web to determine the First Web Contact Angle. Ten droplets, located on the first web, are imaged from which 20 contact angle measurements are performed (one on each side of each imaged droplet), and the arithmetic mean of these 20 contact angle measurements is calculated and reported as the First Web Contact Angle to the nearest 0.1 degree.

The above procedure is used on the first fibrous layer of the second web to determine the Second Web First Fibrous Layer Contact Angle. Ten droplets, located on the first fibrous layer of the second web, are imaged from which 20 contact angle measurements are performed (one on each side of each imaged droplet), and the arithmetic mean of these 20 contact angle measurements is calculated and reported as the Second Web First Fibrous Layer Contact Angle to the nearest 0.1 degree. The ten droplets are analyzed from portions of fibers located within a distance from the first surface of the second web, wherein such distance is 20% of the second web caliper.

The above procedure is used on the second fibrous layer of the second web to determine the Second Web Second Fibrous Layer Contact Angle. Ten droplets, located on the second fibrous layer of the second web, are imaged from which 20 contact angle measurements are performed (one on each side of each imaged droplet), and the arithmetic mean of these 20 contact angle measurements is calculated and reported as the Second Web Second Fibrous Layer Contact Angle to the nearest 0.1 degree. The ten droplets are analyzed from portions of fibers located within a distance from the second surface of the second web, wherein such distance is 20% of the second web caliper.

Average Surface Area/Volume Test Method

The Average Surface Area Per Volume Method uses analysis with a scanning electron microscope (SEM) to determine the average surface area per volume of each of one or more fibrous layers present in a web as well as to determine the average surface area per volume of a web (such as the first web) as whole. SEM images containing front-face views and/or cross-sections of fibers are used to measure the perimeter per cross sectional area of individual fibers, which is deemed to correspond directly to the surface area per volume ratio of these same fibers, from which average surface area per volume present in each layer or web, respectively, is determined.

A rectangular specimen of the web, measuring 1 cm×2 cm, is removed from the elastic laminate of a wearable article taking care not to disturb the structure of the material. The specimen has a length of (2 cm) aligned with a longitudinal centerline of the wearable article. The specimen of interest may be separated from the other components of the wearable article such as the first web and the second web (which may represent the inner web or the outer web of the elastic laminate if used as an elastic belt), elastic bodies between the inner and outer web, or backsheet or any other material by techniques such as applying freeze spray, or other suitable methods that do not permanently alter the properties of the web. The extracted web specimen is conditioned at a temperature of 23±2° C. and a relative humidity of 50±10% for at least 24 hours. The specimen is handled gently throughout by the edges using forceps and is mounted flat on an SEM specimen holder using double-sided tape. Multiple specimens are prepared in similar fashion as needed to accumulate the number of measurements. In instances in which cross sectional analysis is performed, as described below, a new single-edged razor blade (such as 0.009" (0.22 mm) thick surgical carbon steel razor blade (part number 55411-050 from VWR, Radnor, PA, USA, or equivalent) is used to cross-section the specimen prior to mounting in the 2-cm dimension, and one of the fresh cross-sectional faces is subsequently analyzed in the SEM. Prior to introduction into the SEM, each specimen is sputtered with gold or a palladium compound to avoid electric charging and vibrations of the fibers in the electron beam A scanning electron microscope (SEM) is used to analyze the top view and cross section of the fibers.

A magnification of 500 to 10,000 times is chosen such that the ratio of target fiber perimeter to Horizontal Field Width (HFW) is bigger than 0.5. Secondary electron images are acquired with a standard Everhart-Thornley detector.

An initial cross-sectional SEM image of the web of interest is capture. If fibers present have a circular cross-section, then fiber-width measurements from top view images can be used as diameter, and corresponding perimeters (circumferences) are calculated for each diameter assuming circular cross sections. No fiber is measured more than once, and surface area to volume of each fiber measured is recorded as the circumference-to-area ratio at this point of measurement, i.e. $\pi D/((\pi D2)/4)=4/D$, where D is the measured diameter of the fiber. If fibers present in the web do not have a circular cross-section, the area and perimeter for each fiber analyzed are directly measured from SEM cross-sectional web images. The use of image analysis software, such as Image J (NIH, Bethesda, MD, USA, or equivalent) may be used to aid in the accurate and facile measurement of cross-sectional perimeters. The perimeter and area of each cross section measured is recorded, as is the ratio of perimeter to area for each cross section.

If the web of interest exhibits a gradient in fiber size and/or shape, each distinct fibrous layer is separately characterized.

At least 100 measurements of individual fibers are performed for each fibrous layer in the web of interest, or in the web as a whole. The arithmetic mean of the ratios of cross-sectional perimeter to area recorded among fibers in each layer present is calculated, and this is reported as the average surface area per volume of that fibrous layer in the web of interest, or of the fibrous layer or web, respectively, of interest. The average surface area to volume ratio is reported in l/mm to the nearest 0.1 l/mm Fiber Diameter Method The average equivalent fiber diameter of each of one or more distinct fiber(s) layer present in a web is done following the Average Surface Area Per Volume Method. Once the average surface area per volume (SApV) has been determined for a given fiber(s) layer, the average equivalent diameter for that fiber(s) layer is calculated as 4/SApV. The average equivalent fiber diameter is reported in micrometers (µm), to the nearest 0.1 µm.

Effective Opening Area and Opening Rate

Effective Opening Area and Opening Rate measurements are obtained by analyzing images of either an outer web or an inner web specimen independently, or both overlaying each other. Specimen images are generated using an optical microscope such as a Keyence 3D Measurement System VR-3200, or equivalent. Image analysis is performed using ImageJ software (version 1.46 or above, National Institutes of Health, USA, or equivalent). The specimen image needs to be distance calibrated with an image of a ruler to determine the image resolution, i.e., 42.4 pixels per mm. The web specimen is backed with a black material prior to acquiring the image. A total of five replicate specimens are prepared for analysis.

Following the instrument manufacturer's recommended procedures, auto-focus the microscope and acquire a specimen image with a field of view size of 50 mm by 50 mm at a resolution of approximately 42.4 pixels per mm. In like fashion acquire images of the remaining four replicates.

Open a specimen image in ImageJ Set the scale according to the resolution of the calibrated ruler image. Convert the image type to 8 bit. Using the minimum auto threshold, the 8-bit grayscale image is then converted to a binary image (with "zero" or "black" corresponding to the aperture regions) in the following way: If the histogram of gray level (GL) values (ranging from 0 to 255, one bin with propensity $P_i$ per gray level i) has exactly two local maxima, the threshold gray level value t is defined as that value for which $P_{t-1}>P_t$ and $P_t \leq P_{t+1}$. If the histogram has greater than two local maxima, the histogram is iteratively smoothed using a windowed arithmetic mean of size 3, and this smoothing is performed iteratively until exactly two local maxima exist. The threshold gray level value t is defined as that value for which $P_{t-1}>P_t$ and $P_t \leq P_{t+1}$. This procedure identifies the gray level (GL) value for the minimum population located between the dark pixel peak of the aperture holes (openings) and the lighter pixel peak of the specimen material.

Remove outliers before measurement by setting the opening exclusion limit to 10 pixels in radius for dark outliers and 2 pixels in radius for bright outliers. Select the Analyze Particles function. Set the analysis to exclude the partial edge openings and calculate the average opening area via dividing the total area of all included openings by the number of openings, and record as the Effective Opening Area to the nearest 0.1 mm². Add up all the opening area values from the image, including both full and partial openings, and divide the sum by the total area of the field of view of the image, and record as the Opening Rate (%) to the nearest 0.1%. In like fashion analyze the remaining 4 specimen images. Calculate and report the average Effective Opening Area to the nearest 0.1 mm² and the average Opening Rate to the nearest 0.1% for the total 5 replicates.

Relative Opening Rate

Relative Opening Rate is the opening rate of the outer web and the inner web combined, compared to the opening rate of the outer web. Before preparation of specimen, the relationship of openings from the outer web and the inner web as the elastic laminate are observed. If the inner web has no openings, the Relative Opening Rate is determined as 0%. If the inner web has openings and the openings from the outer web and the inner web appear to completely or substantially match, the specimen is arranged as A). If the inner web has openings and the openings from the outer web and the inner web appear to partially match or not match, the specimen is arranged as B).

A) The elastic laminate is treated according to the Preparation of specimen above to obtain the inner and outer webs. The inner and outer webs are overlayed such that the openings match each other as much as possible. The overlayed specimen is sent for measurement.

B) The elastic laminate is treated according to the Preparation of specimen above to obtain the inner and outer webs. The inner and outer webs are overlayed in 2 different degrees of overlap of openings, one which has the openings matched as much as possible, and another which has the openings unmatched as much as possible. The 2 types of overlayed specimen are sent for measurement, respectively. The average Relative Opening Rate of the 2 types of overlayed specimen is obtained.

The overlayed specimen are measured in the same manner as specified under "2. Effective Opening Area and Opening Rate" to obtain the Opening Rate of the overlayed specimen.

The Relative Opening Rate is obtained as such. When there is a complete match between the inner web and the outer web, the Relative Opening Rate is 100%.

Relative Opening Rate (%)=Opening Rate of overlayed specimen/Opening Rate of outer web×100

EXAMPLES

The following nonwoven webs were used in the Examples

Nonwoven 1: Hydrophobic spunbond nonwoven (SSS, i.e. three identical spunbond layers); 100% polypropylene; fiber diameter of about 15 µm; basis weight of 15 gsm. The nonwoven has been supplied by Fibertex under the tradename A10150AH.

Nonwoven 2: Hydrophobic carded air-through bonded nonwoven, bicomponent PE/PET 50% PET (core of bicomponent fibers), 50% polyethylene (shell of bicomponent fibers), fiber diameter of about 14.3 µm; basis weight of 20 gsm. The nonwoven has been supplied by Dayuan under the tradename FJ206.

Nonwoven 3: Hydrophilic spunbond nonwoven (SSS, i.e. three identical spunbond layers); 100% polypropylene; fiber diameter of about 16.2 µm; basis weight of 15 gsm. The nonwoven has been supplied by Fibertex under tradename A20150 KV.

Nonwoven 4: Hydrophilic carded air-through bonded nonwoven, bicomponent PE/PET 50% PET, 50% polyethylene, fiber diameter of about 14.8 µm; basis weight of 22 gsm. The nonwoven has been supplied by Yanjan. Under the tradename Z05X-22.

Nonwoven 5: Spunlace nonwoven, total basis weight 30 gsm; first fibrous layer is hydrophobic spunbond nonwoven (SSS), PP, fiber diameter of about 15.1 µm and basis weight of 11 gsm; second fibrous layer is hydrophilic cotton fibers with basis weight of 19 gsm (second fibrous layer is facing towards the outer web). First and second fibrous layers are combined via hydrojets in the spunlace process, such that at least some of the fibers of the second fibrous layer interpenetrate the fibers of the first fibrous layer. The nonwoven has been supplied by Yanj an under tradename FL08-30.

Nonwoven 6: Spunlace nonwoven, made with 100% hydrophilic bamboo viscose fibers, basis weight of 42 gsm. The nonwoven has been supplied by Winson under specification name: Spunlace NW-fullcross-40mesh-bamboo-viscose.

Moreover, the following commercially available absorbent pants products were tested:

GooN Angel Premium Size L, market product with lot number 20190222

The inner belt nonwoven web and the outer belt nonwoven web have been carefully removed from the elastic belt laminate and from the remaining product components.

New Moony Sweat Control Pants Size L, market product with lot number 201903259011

The inner belt nonwoven web and the outer belt nonwoven web have been carefully removed from the elastic belt laminate and from the remaining product components. This product also features a blue tinted patch layer, having dimensions smaller than the inner belt nonwoven web and outer belt nonwoven web. The patch is attached to the inner surface of the elastic laminate such that the patch layer is in direct contact with the wearer's skin in the back side of the product when the article is in use. This patch layer has also been carefully removed from the elastic belt and the remaining product components.

TABLE 1

Vertical Wicking height in mm, measured as function of wicking time for Nonwovens 1-6

| Vertical Wicking Time, sec | Nonwoven 1 | Nonwoven 2 | Nonwoven 3 | Nonwoven 4 | Nonwoven 5 | Nonwoven 6 |
| --- | --- | --- | --- | --- | --- | --- |
| 10 | 0 | 0 | 0 | 0 | 11 | 41 |
| 30 | 0 | 0 | 0 | 0 | 18 | 63 |
| 60 | 0 | 0 | 0 | 0 | 25 | 81 |

TABLE 2

Vertical Wicking Height in mm, measured as function of wicking time for commercial products

| Vertical Wicking Time, sec | GooN Angel Premium Inner Belt | GooN Angel Premium Outer Belt | New Moony Sweat Control Pants Patch Layer | New Moony Sweat Control Pants Inner Belt | New Moony Sweat Control Pants Outer Belt |
|---|---|---|---|---|---|
| 10 | 0 | 0 | 23 | 0 | 0 |
| 30 | 0 | 0 | 30 | 0 | 0 |
| 60 | 0 | 0 | 35 | 0 | 0 |

Partitioning Test

The Partitioning Test was carried out to measure the ability of an elastic laminate to remove sweat from a surface, mimicking the skin of the wearer, to wick the sweat away from inner web into the outer web and to wick the sweat in the plane of the outer web.

The test specimens were formed without elastic strands in between the inner web and the outer web of the elastic laminate, and the inner and outer web were attached to each other with 5 g/m² adhesive applied in spiral pattern. The test specimens were of squared shape with 4 cm dimension.

Three test specimens of each Example were tested.

The test was carried at a temperature of 23° C.±2° C. and a relative humidity of 50%±5%.

The test specimens were conditioned at a temperature of 23° C.±2° C. and a relative humidity of 50%±5% for at least 24 hours.

Test fluid was saline solution (0.9% wt. of NaCl in water solution). A blue dye (Brillant Blue food additive from Jianjin DUOFUYUAN Industrial Co. LTD or equivalent) was added at a concentration of 0.010 g in 20 ml of saline solution.

Ca. 0.12 g of test fluid were loaded as a single drop onto the center of a glass Petri dish (having an inner diameter of at least 9 cm), the actual, exact amount of saline, $M_{fluid}$, was determined via subtracting the dry glass Petri dish weight ($M_{P,D}$) prior to the application of the fluid from the glass Petri dish weight with ca. 0.12 g fluid ($M_{P,L}$):

$$M_{fluid}=M_{P,L}-M_{P,D}$$

The test specimen was laid over the fluid gently, a pressure was applied on top via micro-slide, having a weight of 9.2 g and having dimensions of 5 cm×7.5 cm and a thickness of 0.96 to 1.06 mm. The micro-slide was 2947-75×50, made of glass from Corning Incorporated or equivalent. The inner web of the test specimen was placed in contact with the test fluid. After 1 minute of contact, the sample was removed and the final weight of Petri dish is recorded ($M_{P,F}$): the residual fluid on Petri dish was determined via subtracting the dry glass Petri dish weight, prior to the application of the fluid, from the final glass Petri dish weight:

$$M_{Residual}=M_{P,F}-M_{P,D}$$

The % of Residual Fluid on the Petri dish was calculated as follows:

$$\% \text{ Residual Fluid on Petri dish}=M_{Residual}/M_{fluid}\times100$$
(expressed in %)

The arithmetic mean of the 3 test specimens (per Example) was calculated and reported as the "% of Residual Fluid on the Petri dish" to the nearest 0.1%.

The inner web was separated from the outer web, while the laminate is still wet, and both are hang out for air drying for at least 30 minutes before taking images.

An image of the inner web was taken using HP color scanner, and the Inner Web Wet Area was determined using ImageJ software for processing of the scanned image.

The arithmetic mean of the measurements of the three test specimens (per Example) was calculated and reported as the "Inner Web Wet Area" to the nearest 0.1 mm².

An image of the outer web is taken using HP color scanner, and the Outer Web Wet Area is determined using ImageJ software for processing of the scanned image.

The arithmetic mean of the measurements of the three test specimens (per Example) is calculated and reported as the "Outer Web Wet Area" to the nearest 0.1 mm².

TABLE 3

Results of Partitioning Test

|  | Comparative Example 1 | Comparative Example 2 | Example 1 | Example 2 | Example 3 |
|---|---|---|---|---|---|
| Inner Web | Nonwoven 1 | Nonwoven 1 | Nonwoven 1 | Nonwoven 3 | Nonwoven 3 |
| Outer Web | Nonwoven 2 | Nonwoven 4 | Nonwoven 5 with second fibrous layer oriented towards inner web | Nonwoven 5 with second fibrous layer oriented towards inner web | Nonwoven 6 |
| % Residual Fluid on Petri dish | 90.1% | 45.5% | 16.7% | 7.4% | 1.4% |
| Inner Web Wet Area, mm² | 4.0 | 129.6 | 3.7 | 265.6 | 0 |
| Outer Web Wet Area, mm² | 0 | 156.3 | 907.2 | 944.0 | 1373.3 |

Examples 1-3 featuring a second web as outer web which has a vertical wicking height after 60 seconds which is considerably higher than the vertical wicking height after 60 second of the inner web (=first web) exhibit substantially better transport of liquid from the Petri dish compared to Comparative Examples 1 and 2, as is reflected by very low percentage of Residual Fluid on Petri dish in Examples 1-3.

Moreover, transport away from the web which is in direct contact with the fluid (and in direct contact with the skin of the wearer in use conditions of the wearable article) is substantially better for Examples 1-3 vs. Comparative Examples 1 and 2, as is shown by large size of wet area for the outer web relative to the inner web.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm" Further, every numerical range given throughout this specification includes every narrower numerical range that falls within such broader numerical range.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A wearable article comprising an elastic laminate, the elastic laminate comprising a first web and a second web being in a face to face relationship with each other, each of the first and second web being comprised by the complete surface area of the elastic laminate wherein the first web is a nonwoven web having a vertical wicking height after 60 seconds of less than 5 mm according to a Vertical Wicking Height Test Method, and wherein the second web is a nonwoven web having a vertical wicking height after 60 seconds of at least 5 mm according to the Vertical Wicking Height Test Method; and
  wherein a plurality of elastic strands is provided between the first and second web.

2. The wearable article of claim 1, wherein the first web has a vertical wicking height after 60 seconds being at least 5 mm lower than the vertical wicking height of the second web.

3. The wearable article of claim 1, wherein the first web comprises at least 90 weight-% of synthetic fibers based on the total weight of the first web.

4. The wearable article of claim 3, wherein the synthetic fibers of the first web are selected from the group consisting of polyethylene, polypropylene, polyester, polylactic acid, and mixtures and combinations thereof.

5. The wearable article of claim 1, wherein the second web comprises at least 20 weight-% of natural fibers.

6. The wearable article of claim 5, wherein the natural fibers are natural hydrophilic fibers and are selected from the group consisting of cotton, bamboo, viscose, cellulose, silk, or mixtures or combinations thereof.

7. The wearable article of claim 5, wherein the second web further comprises synthetic fibers and wherein the natural fibers and synthetic fibers are mixed.

8. The wearable article of claim 1, wherein the article has a longitudinal direction and a transverse direction, wherein, in the elastic laminate, the elastic strands extend along the transverse direction and are spaced apart from each other in the longitudinal direction of the article.

9. A wearable article comprising an elastic laminate, the elastic laminate comprising a first web and a second web being in a face to face relationship with each other, each of the first and second web being comprised by the complete surface area of the elastic laminate wherein the first web is a nonwoven web having a vertical wicking height after 60 seconds of less than 5 mm according to a Vertical Wicking Height Test Method, and wherein the second web is a nonwoven web having a vertical wicking height after 60 seconds of at least 5 mm according to the Vertical Wicking Height Test Method; and
  wherein the second web is formed of a first fibrous layer forming a first surface of the second web and a second fibrous layer forming a second surface of the second web, wherein the fibers of the first fibrous layer are synthetic fibers and the fibers of the second fibrous layer are natural fibers, wherein the first and second fibrous layer are integrally combined with each other, and wherein at least a part of the natural fibers interpenetrate the fibers of the first fibrous layer.

10. The wearable article of claim 9, wherein at least some of the fibers of the second fibrous layer interpenetrate the fibers of the first fibrous layer such that they protrude out of the first surface of the second web.

11. The wearable article of claim 9, wherein the second web has a thickness and the first fibrous layer forms a first surface of the second web and the second fibrous layer forms a second surface of the second web, wherein the amount of natural fibers gradually increases through the thickness from the first surface towards the second surface of the second web.

12. The wearable article of claim 11, wherein the second surface of the second web faces towards the first web, and the first surface of the second web faces away from the first web.

13. A wearable article comprising an elastic laminate, the elastic laminate comprising a first web and a second web being in a face to face relationship with each other, each of the first and second web being comprised by the complete surface area of the elastic laminate wherein the first web is a nonwoven web having a vertical wicking height after 60 seconds of less than 5 mm according to a Vertical Wicking Height Test Method, and wherein the second web is a nonwoven web having a vertical wicking height after 60 seconds of at least 5 mm according to the Vertical Wicking Height Test Method; and
  wherein the first and second web are both non-elastic.

14. A wearable article comprising an elastic laminate, the elastic laminate comprising a first web and a second web being in a face to face relationship with each other, each of the first and second web being comprised by the complete surface area of the elastic laminate wherein the first web is a nonwoven web having a vertical wicking height after 60 seconds of less than 5 mm according to a Vertical Wicking Height Test Method, and wherein the second web is a nonwoven web having a vertical wicking height after 60 seconds of at least 5 mm according to the Vertical Wicking Height Test Method; and wherein the wearable article has a longitudinal direction with a longitudinal centerline and extending from a front waist edge to a back waist edge, and a transverse direction with a transverse centerline and extending perpendicular to the longitudinal direction, the wearable article comprising an elastic belt, the elastic belt being formed by the elastic laminate, the elastic belt having a front belt and a back belt which are discontinuous in the longitudinal direction of the article and wherein left and right transverse edges of the front belt and the back belt are joined by side seams to form two leg opening and such that the front and back waist edge jointly form a continuous waist opening, the left and right transverse edges extending substantially parallel to the longitudinal direction of the article.

15. The wearable article of claim 14, wherein the first web of the elastic laminate constitutes an inner web of the elastic belt, such that at least a portion of the first web is in direct contact with the skin of the wearer, when the article is in use, and the second web forms an outer web of the elastic laminate.

16. The wearable article of claim 14, wherein the front belt forms a front waist region and the back belt forms a back waist region of the wearable article, the front waist region having the front waist edge and a front proximal edge defined by the front belt, the longitudinal dimension of the front belt being the distance between the front waist edge and the front proximal edge parallel to the longitudinal centerline, and back waist region having the back waist edge and a back proximal edge defined by the back belt, the longitudinal dimension of the back belt being the distance between the back waist edge and the back proximal edge parallel to the longitudinal centerline;

the front and back waist edge each comprising a fold over region wherein the second web is extended beyond the elastic laminate, and the extended portion of the second web is folded over the elastic laminate, such that at least a portion of the elastic belt comprises the first web sandwiched between the second web and the folded over, extended portion of the second web, and wherein the folded over, extended portion of the second web is in direct contact with the skin of the wearer when the wearable article is in use, the fold line formed upon folding over the extended portion of the second web forming the front and back waist edge of the article, wherein, in the front belt, the longitudinal extension of the extended, folded over portion of the outer web has a dimension along the longitudinal direction of the wearable article which is less than 35% of the longitudinal dimension of the front belt, and, wherein, in the back belt, the longitudinal extension of the extended folded over portion has a dimension along the longitudinal direction of the wearable article which is less than 35% of the longitudinal dimension of the back belt.

17. The wearable article of claim 14, the wearable article further comprising a central chassis; the center of the front belt being joined to a front waist panel of the central chassis, the center of the back belt being joined to a back waist panel of the central chassis, and the remainder of the central chassis forming a crotch region, the front and back belt each having a left side panel and a right side panel where the central chassis does not overlap.

* * * * *